(12) United States Patent
Szoka, Jr. et al.

(10) Patent No.: US 6,300,317 B1
(45) Date of Patent: *Oct. 9, 2001

(54) SELF-ASSEMBLING POLYNUCLEOTIDE DELIVERY SYSTEM

(75) Inventors: Francis C. Szoka, Jr.; Jean Haensler, both of San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/469,899

(22) Filed: Jun. 6, 1995

Related U.S. Application Data

(63) Continuation of application No. 07/913,669, filed on Jul. 14, 1992, now abandoned, which is a continuation-in-part of application No. 07/864,876, filed on Apr. 3, 1992, now abandoned.

(51) Int. Cl.[7] .................................................. A61K 48/00
(52) U.S. Cl. ............................ 514/44; 435/440; 435/443; 435/455; 435/458
(58) Field of Search ................................. 435/172.3, 440, 435/443, 455, 458; 514/44; 536/23.1

(56) References Cited

U.S. PATENT DOCUMENTS

| | | | |
|---|---|---|---|
| 4,394,448 | 7/1983 | Szoka et al. | 435/172.3 |
| 4,897,355 | 1/1990 | Eppstein et al. | 435/240.2 |
| 4,946,787 | 8/1990 | Epstein et al. | 435/240.2 |
| 5,013,556 | 5/1991 | Woodle et al. | 424/450 |
| 5,166,320 | * 11/1992 | Wu et al. | 530/395 |
| 5,714,166 | * 2/1998 | Tomalia et al. | 424/486 |

FOREIGN PATENT DOCUMENTS

| | | | |
|---|---|---|---|
| 8702061 | * 4/1987 | (WO) | C12P/21/00 |
| 9009786 | * 9/1990 | (WO) | A61K/31/100 |
| 9104753 | * 4/1991 | (WO) | A61K/47/48 |
| 9107947 | * 6/1991 | (WO) | A61K/9/08 |
| 9115501 | * 10/1991 | (WO) | C07H/21/02 |
| 9222635 | * 12/1992 | (WO) | A61K/47/48 |
| 9305162 | * 3/1993 | (WO) | C12N/15/63 |

OTHER PUBLICATIONS

Takahashi et al., Biochemica et Biophysica Acta, vol. 1069, pp. 229–234, 1991.*
Caminati et al. (1990), J. Amer. Chem. Soc. 112:8515–8522.*
Legendre et al. (1992), Pharmaceutical Res. 9(10):1235–1242.*
Legendre et al. (1993), Proc. Natl. Acad. Sci. USA 90: 893–897.*
O'Conner et al. (1985), Biochem. Biophys. Acta 817: 95–102.*
Zhu et al. (1990), Plant Cell, Tissue & Organ Culture 22: 135–145.*
Haensler et al. (1993), Bioconjugate Chem. 4: 85–93.*
Cotten et al. (1990), Proc. Natl. Acad. Sci USA 87: 4033–4037.*
Ledley (1991), Human Gene Therapy 2: 77–83.*
Bentz, J. et al., "Destabilization of Phosphatidylethanolamine–Containing Liposomes: Hexagonal Phase and Asymmetric Membranes", *Biochemistry* 26:2105–2116 (1987).

(List continued on next page.)

Primary Examiner—Ardin H. Marschel
(74) Attorney, Agent, or Firm—Nathan P. Koenig; Crosby, Heafey, Roach & May

(57) ABSTRACT

This invention provides a self-assembling polynucleotide delivery system comprising components aiding in the delivery of the polynucleotide to the desired address which are associated via noncovalent interactions with the polynucleotide. The components of this system include DNA-masking components, cell recognition components, charge-neutralization and membrane-permeabilization components, and subcellular localization components. Specific compounds useful in this system are also provided.

67 Claims, 12 Drawing Sheets

OTHER PUBLICATIONS

Bergstrom, S. et al., *Acta Chem. Scand.* 7:1126 (1953).
Bout et al., "Abstracts of the 1991 Cystic Fibrosis Conference," Abst. No. 87 (1991).
Chu, C.–J. et al., *Pharmacent Res.* 7:824–834 (1990).
Cornetta, K. et al. *Human Gene Ther.* 2:3 (1991).
Felgner, P.L., *Adv. Drug Delivery Rev.* 5:163 (1990).
Haensler, J., et al., *Biochem. Biophys. Acta* 946:95–105 (1988).
Karup, G. et al., *Int. J. Peptide Protein Res.* 32:331–343 (1988).
Krauss, E. et al., *Biochemistry* 22:4280–4291 (1983).
Larwood, D. and F. Szoka, *J. Labelled Comp. & Radiopharm* 21:603–614 (1984).
McPherson, M. et al., Molecular and Cellular Biology of Cystic Fibrosis;, *Molec. Aspects Med.* 12L1–81 (1991).
Parente, R. et al., *Biochemistry* 29:8713–8719 (1990).
Parente, R. et al., *Biochemistry* 29:8720–8728 (1990).
Pidgeon, C. et al., *Anal. Biochem.* 176:36–47 (1989).
Ponpipom, M.M. et al., *J. Med. Chem.* 24:1388–1395 (1981).
Wagner, E. et al., "DNA–binding transferrin conjugates as functional gene–delivery agents: Synthesis by linkage of polylysine or ethidium homodimer to the transferrin carbohydrate moiety", *Bioconjugate Chem.* 2:226–231 (1991).
Wagner, E. et al., "Transferrin–polycation–DNA complexes: The effect of polycations on the structure of the complex and DNA delivery to cells", *Proc. Natl. Acad. Sci. (USA)* 88:4255–4259 (1991).
Wang, C.Y., et al., *Biochemistry* 28:9508–9514 (1989).
Wu, E. et al., *Biochemistry,* 17:5543–5550 (1978).
Riordan, J.R., et al., Science 245:1066 (1989).
Karem, B., et al., Science 245:1073 (1989).
Friedman, T., Science 244:1275 (1989).
Bluestone, M., Botechnol. 10:132 (1992).
Rosenfeld, M.A., et al., Cell 68:143 (1992).
Rosenfeld, M.A., et al., Science 252:431 (1991).
Felgner, P.L., et al., Nature 349:351 (1991).
Capecchi, M.R., Cell 22:479 (1980).
Nicolau, C., et al., Crit. Rev. Ther. Drugg Carr., Sys. 6:239 (1989).
Mannio, R.J, et al., Biotechniques 6:682 (1988).
Felgner, P.L., et al., P.N.A.S. (USA) 84:7413 (1987).
Lu, L., et al., Pflugers Arch. 415:198 (1989).
Hazinski, T.A., et al., Am. J. Espir. Cell Mol. Biol. 4:206 (1991).
Brigham, K.L., et al., Am. J. Med. Sci. 298:278 (1989).
Loeffler, J., et al., J. Neurochem. 54:1812 (1990).
Zhou, X., et al., Biochem. Biophys .Acta 1065:8 (1991).
Gao, X., et al., Biochim. Biophys. Res. Comm. 179:280 (1991).
Düzgünes, N., Biochem. 28:9179 (1989).
Lai, M.Z., et al, Biochem. 24:1646 (1985).
Wu, G.Y., et al., J. Biol. Chem. 262:4429 (1987).
Wu, G.Y., et al., J. Biol. Chem. 263:14621 (1988).
Huckett, et al., Biochem. Pharmacol., 40:253 (1990).
Wagner, et al., P.N.A.S. (USA) 87:3410 (1990).
Curiel, D.T., e t al., P.N.A.S. (USA), 88:8850 (1991).
Behr, J.P., Tet. Lett. 27:5861 (1986).
Dingwall , C., et al., TIBS 16:478 (1991).
Kaneda, Y., et al., Science 243:375 (1989).
Silver, P.A., Cell 64:489 (1991).
Finlay, D.R., et al., J. Cell Sci. Supp. 11:225 (1989).
Tikchonenko, T.I., et al., Gene 63:321 (1988).
Böttger, M., et al., Biochem. Biophys. Acta 950:221 (1988).
Nielsen, P.E., Eur. J. Biochem. 122:283 (1982).
Ellens et al., Biochem. 25:285 (1986).

\* cited by examiner

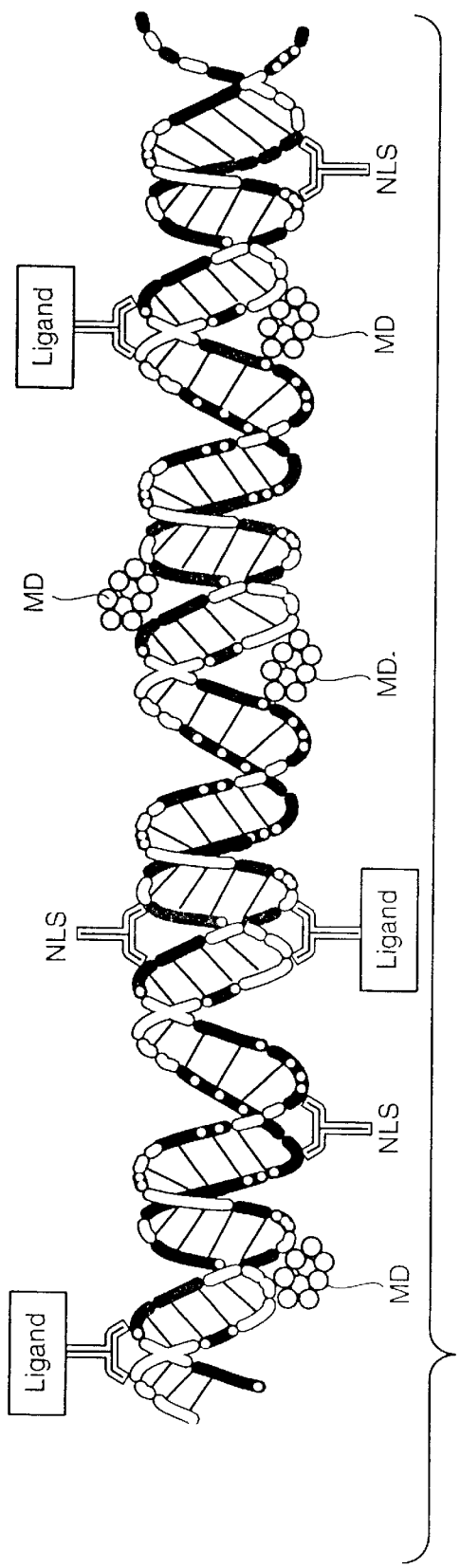
FIG._1
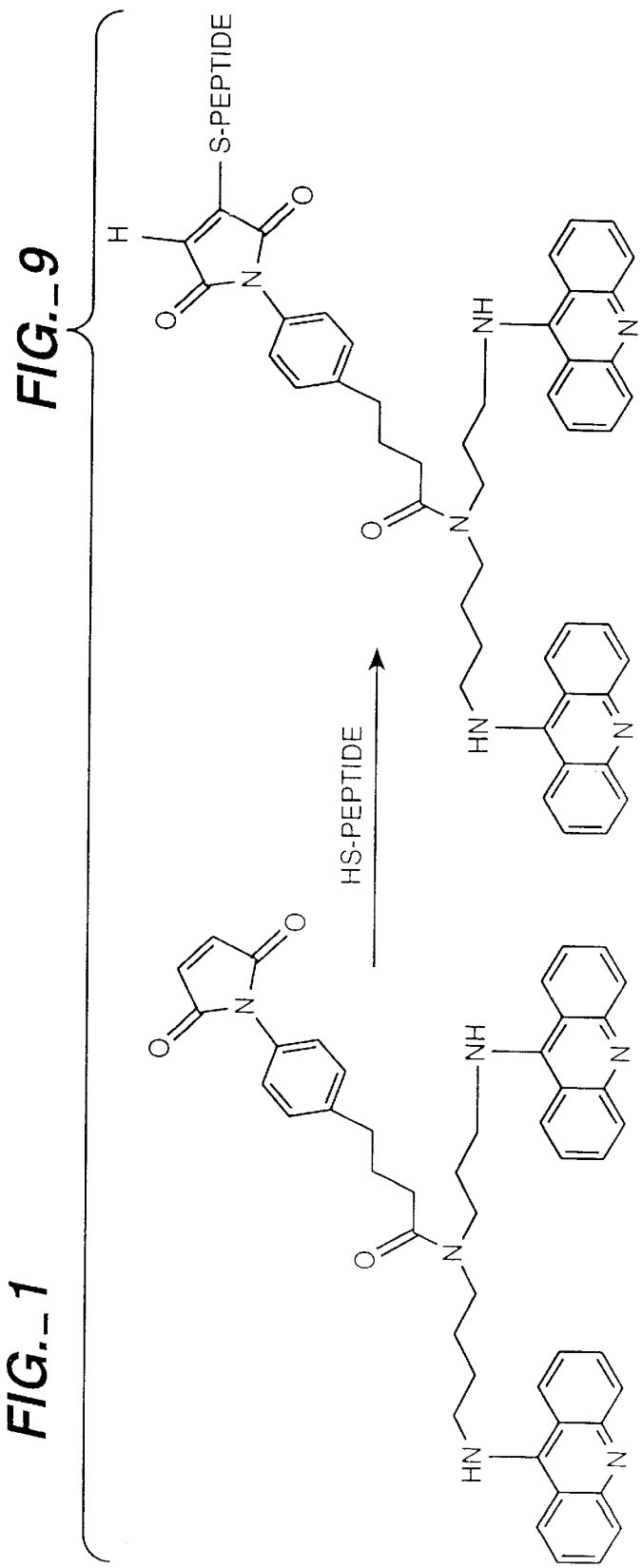
FIG._9

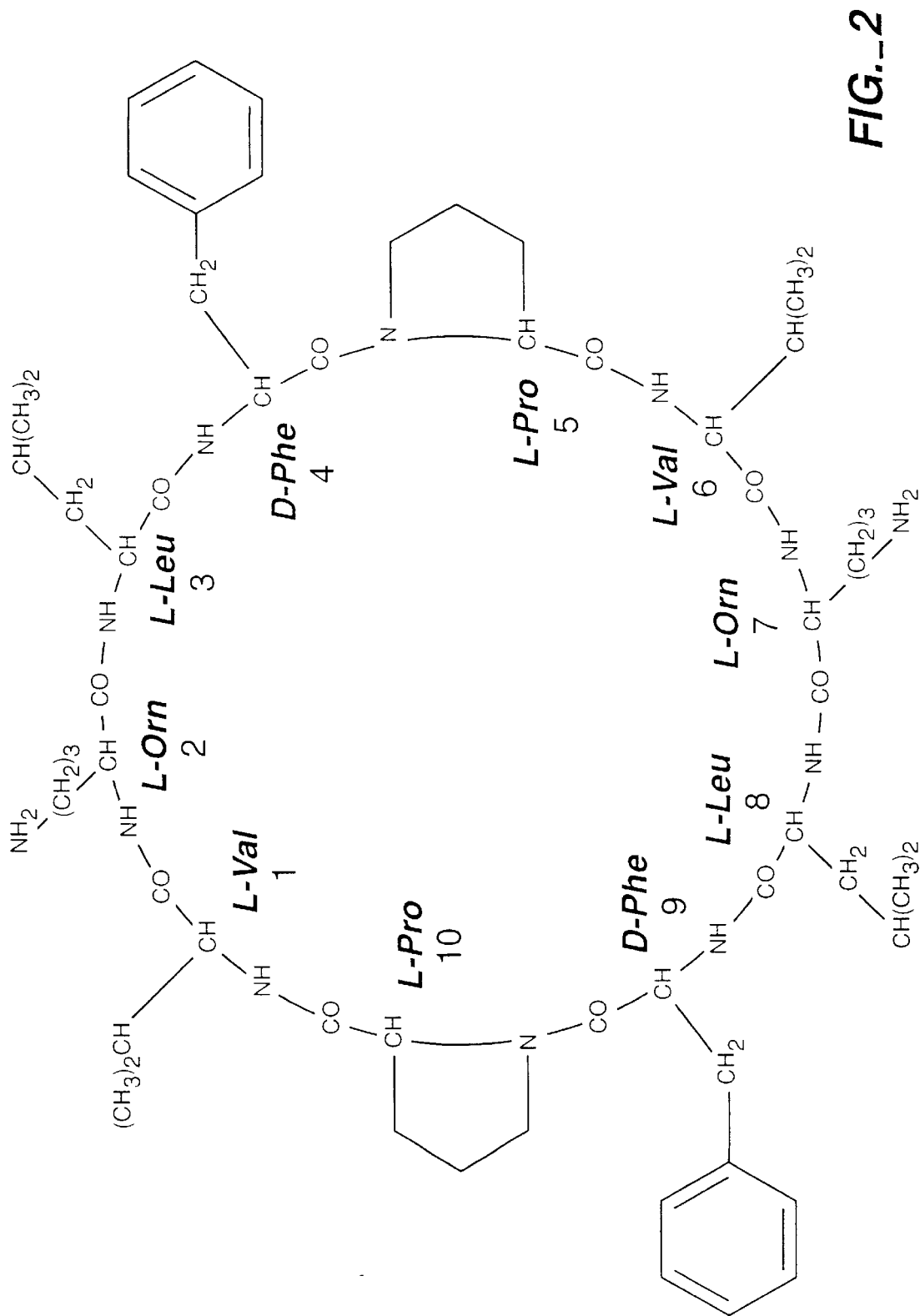
FIG._2

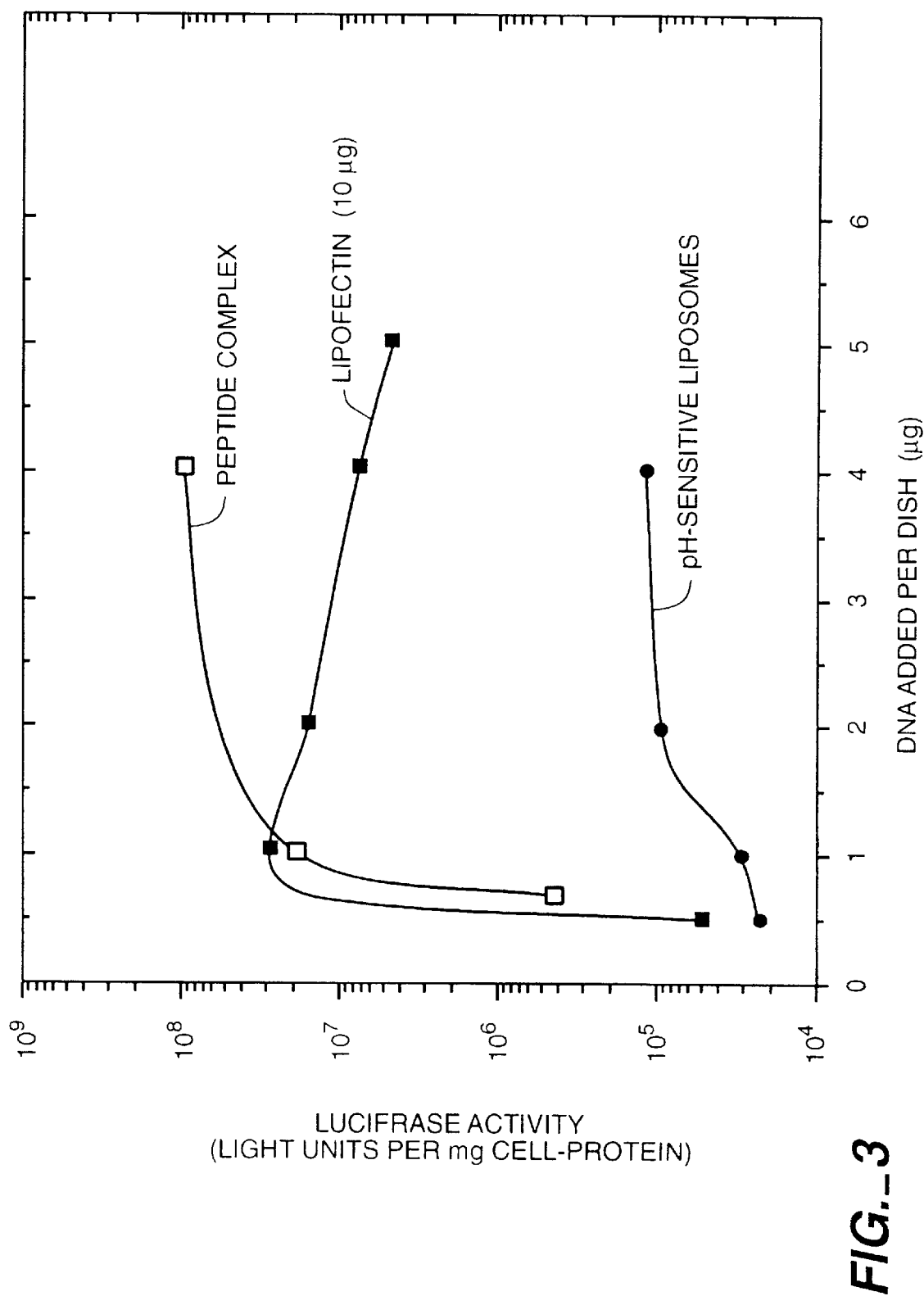
FIG._3

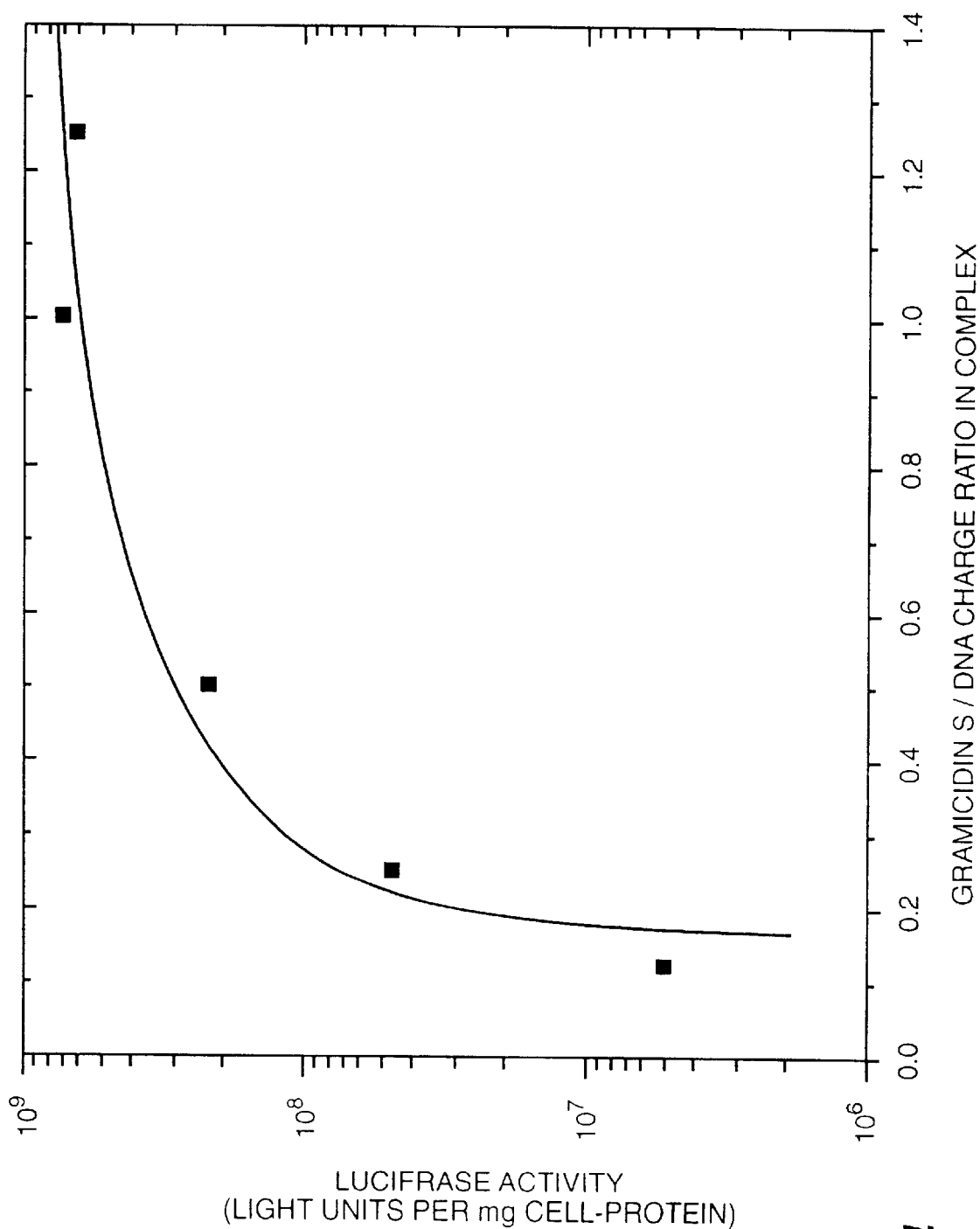
FIG._4

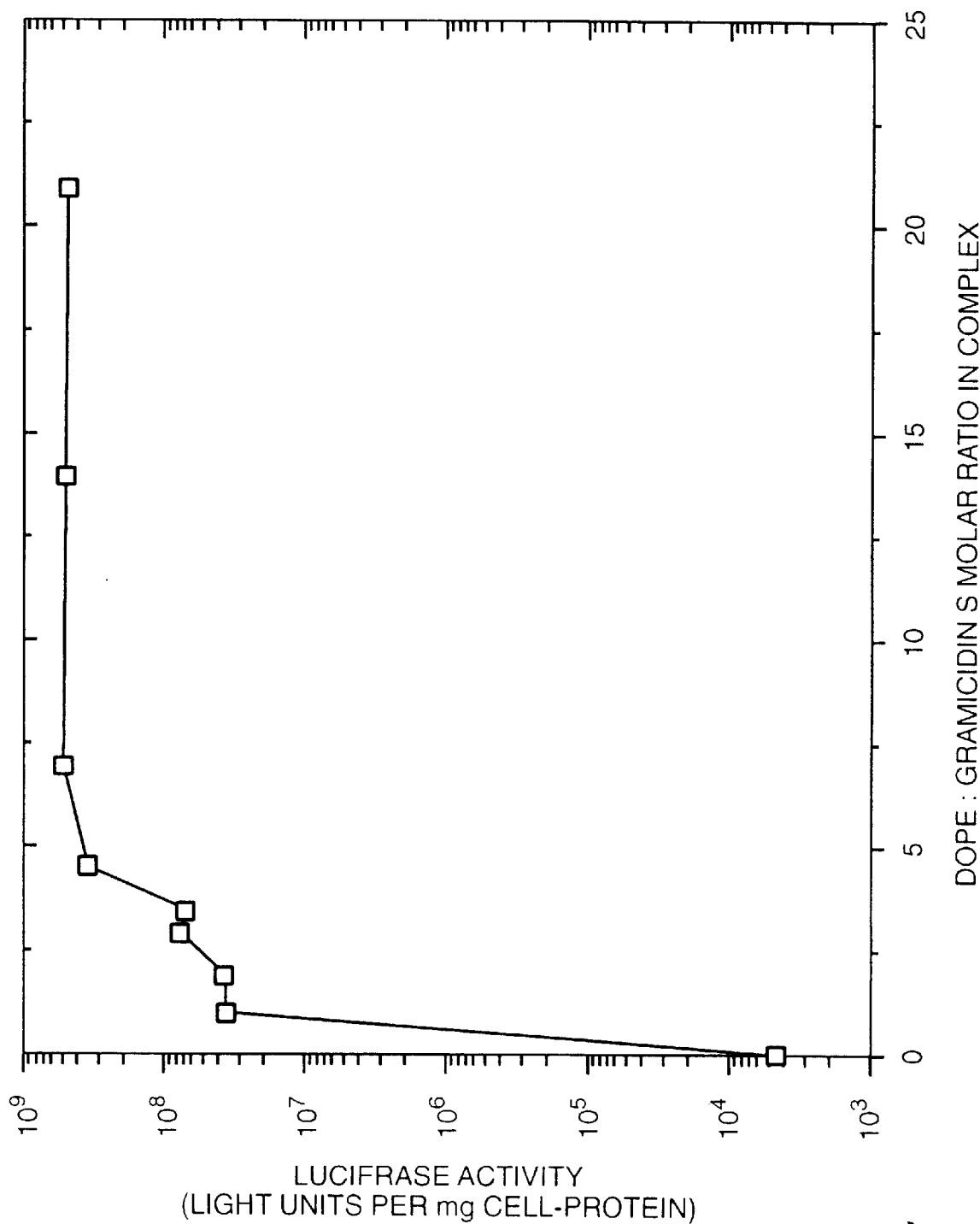
FIG._5

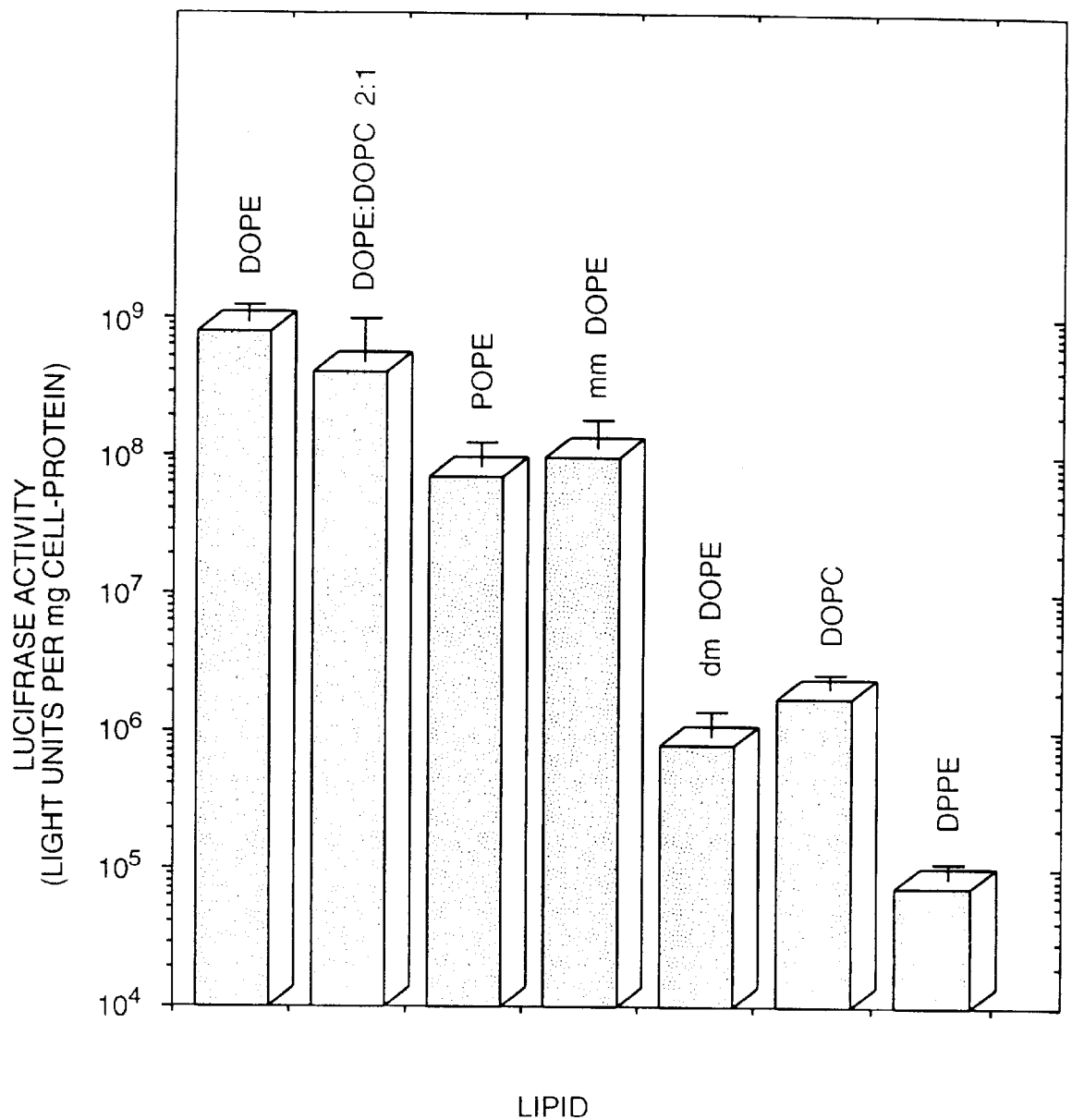
FIG._6

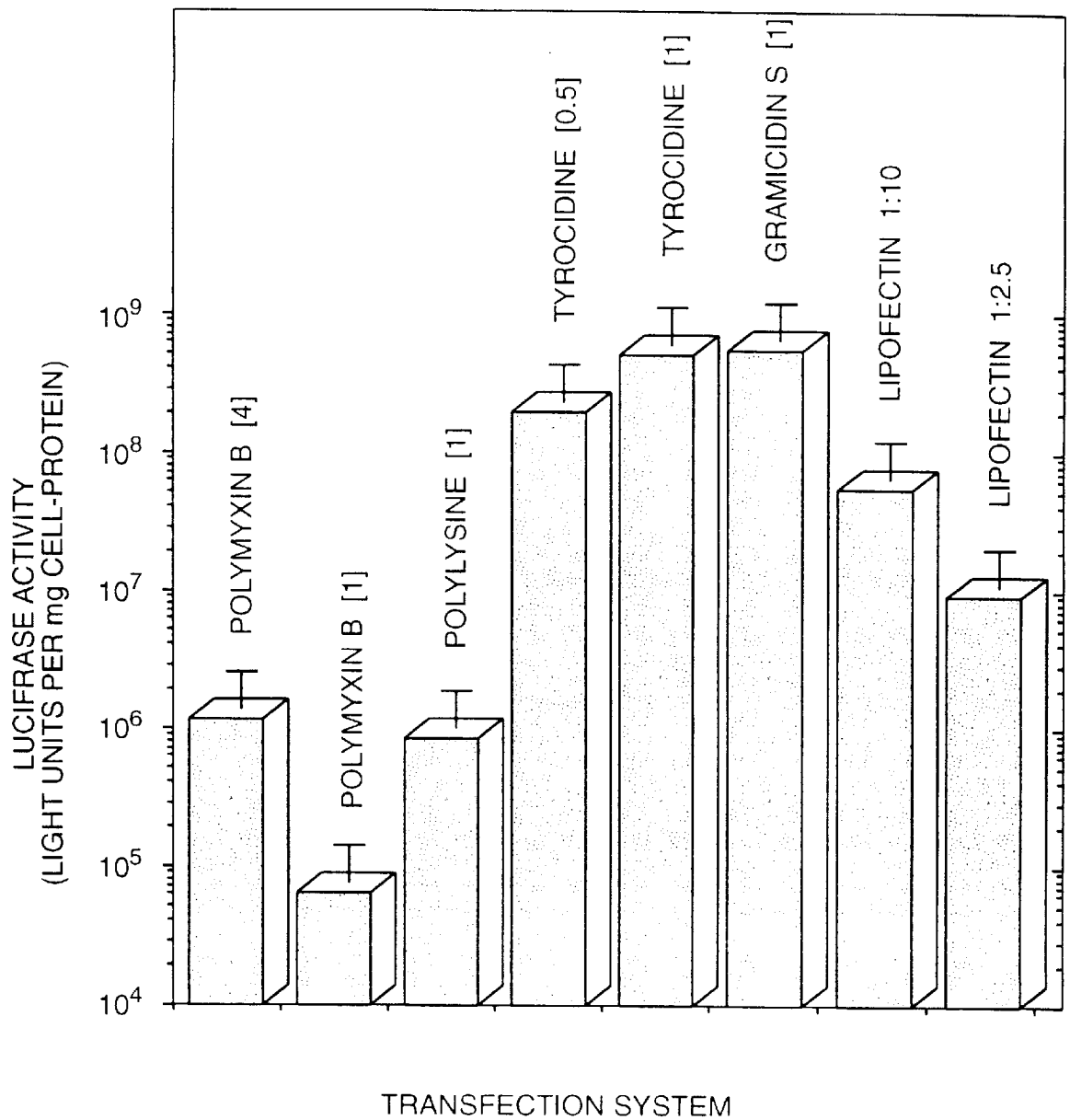
FIG._7

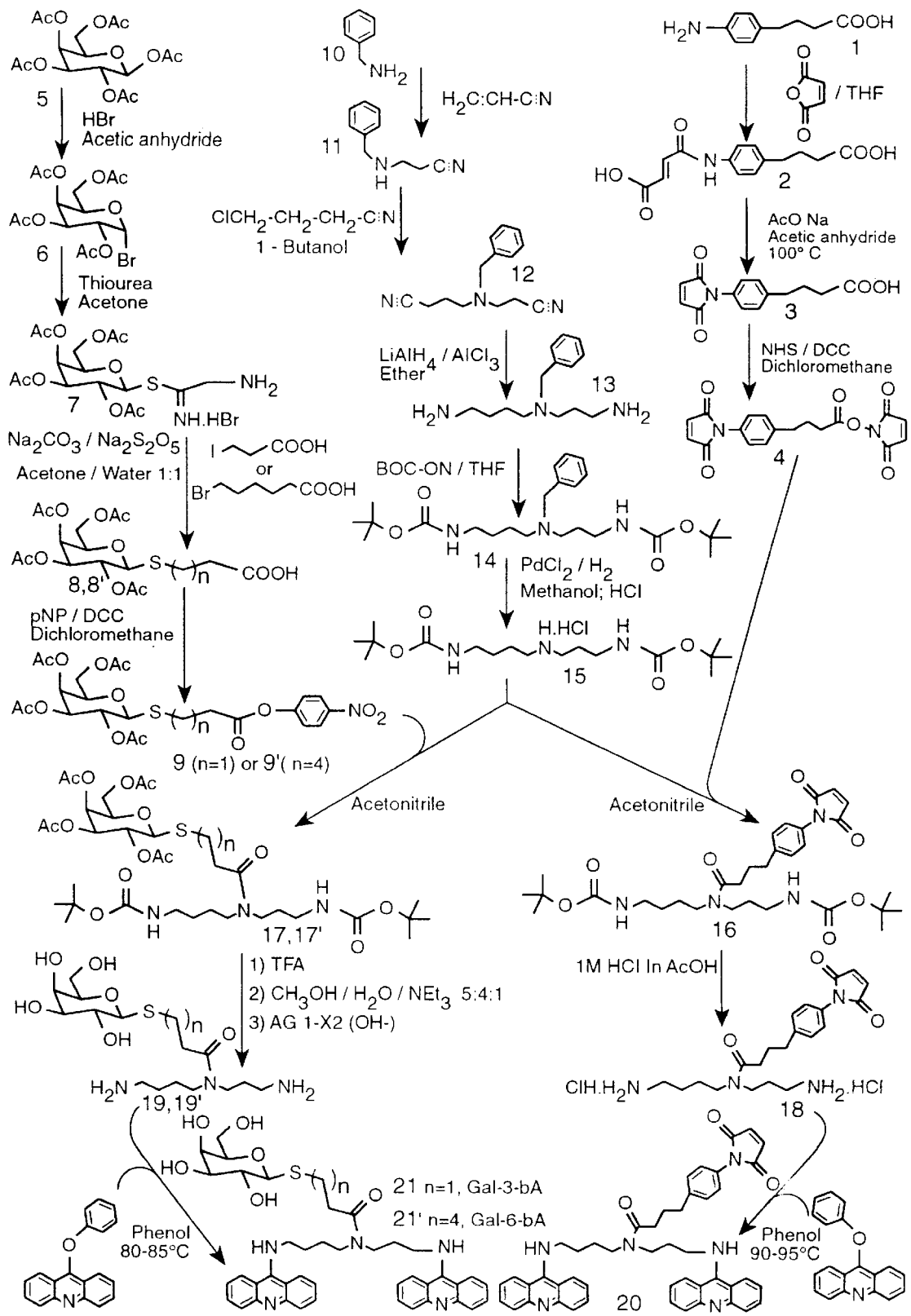
FIG._8

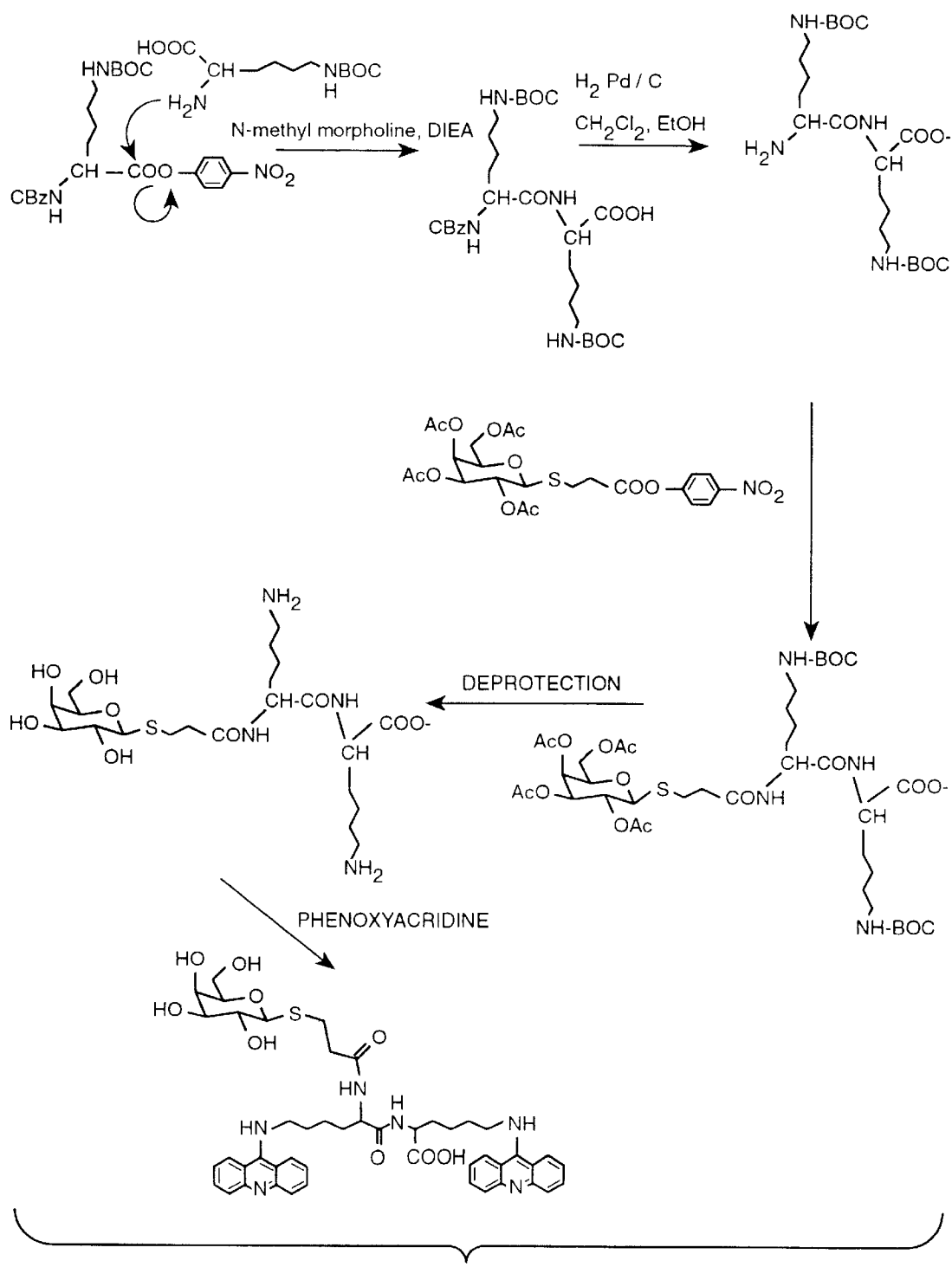
FIG._10

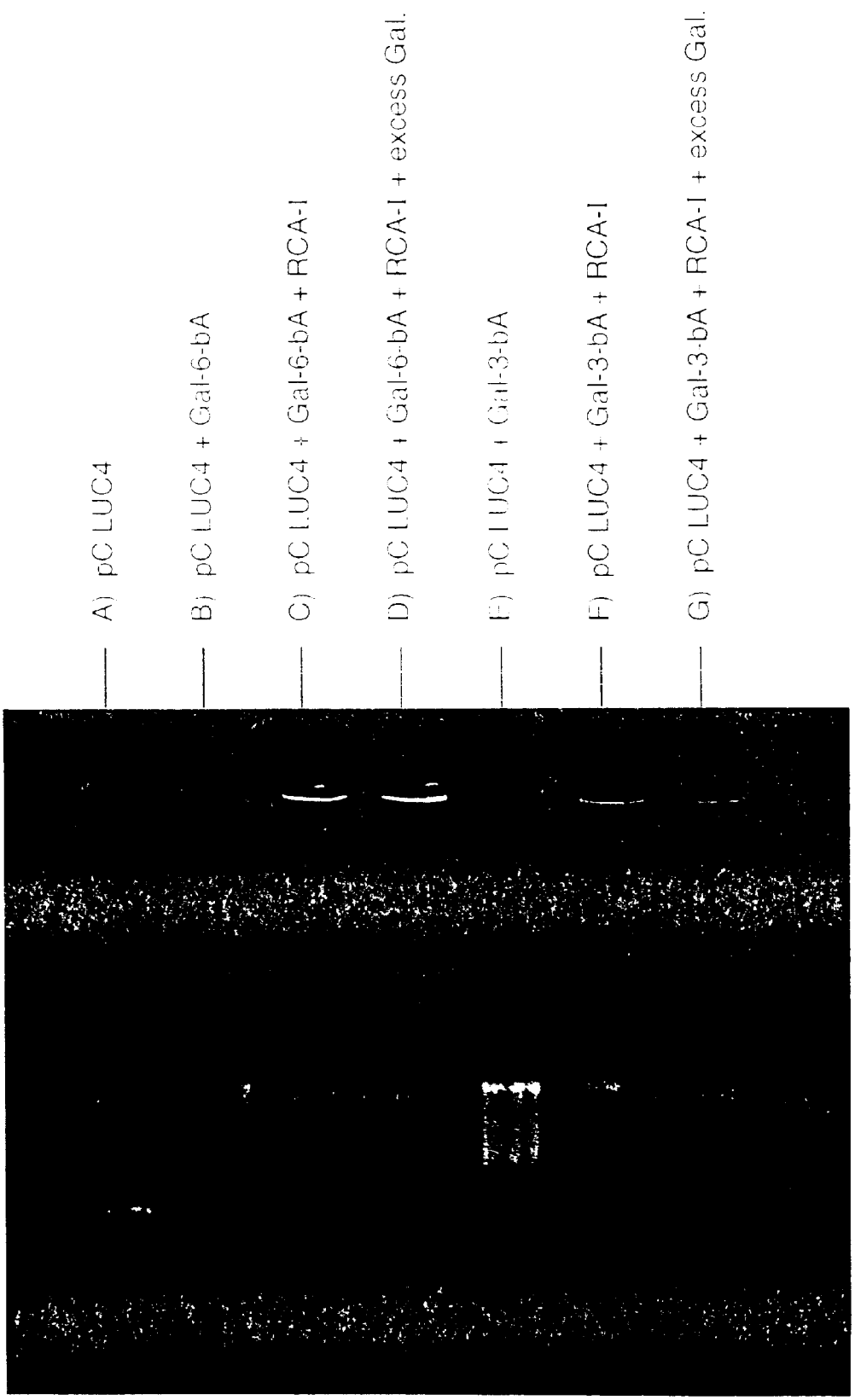
FIG._11

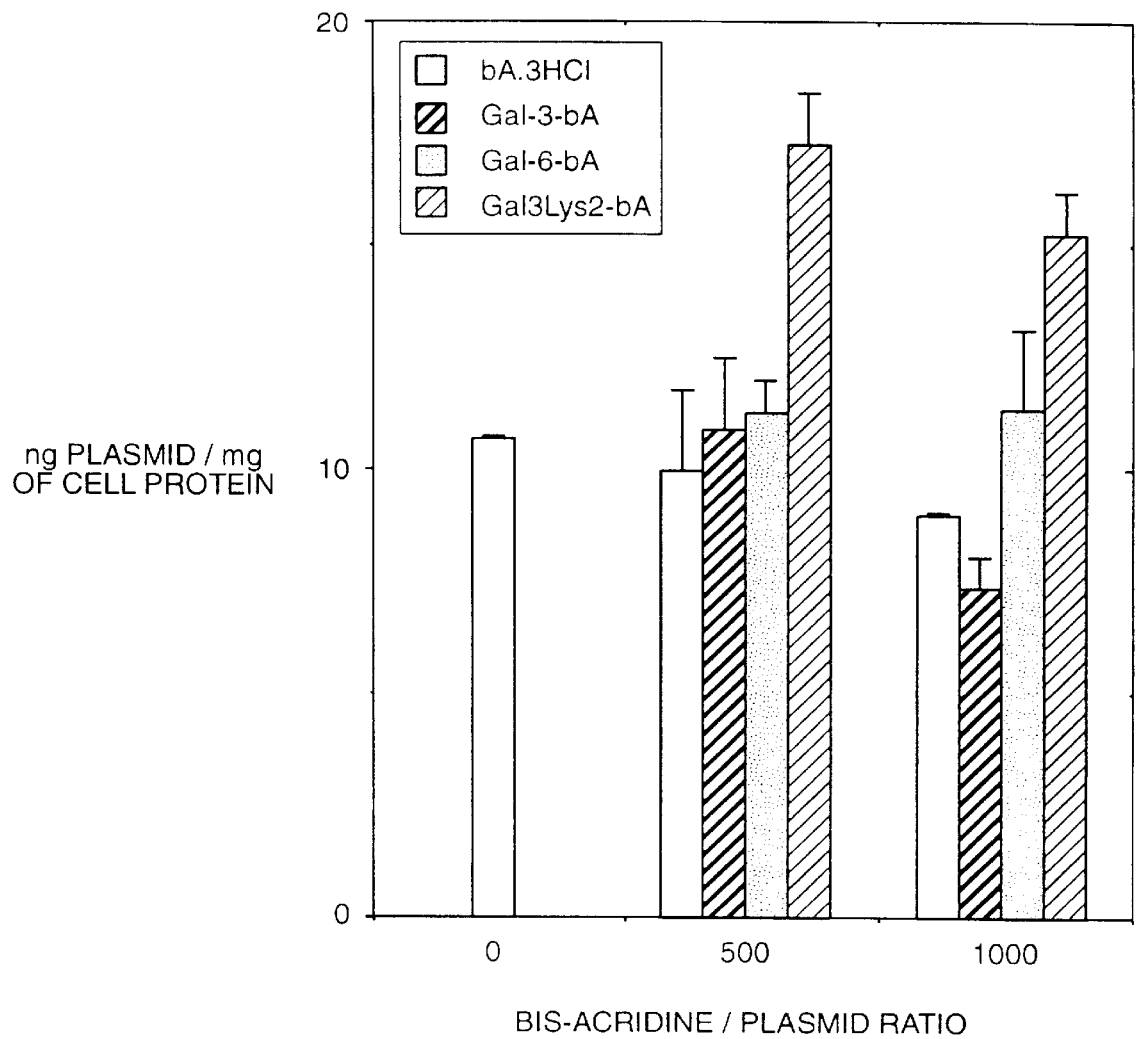
FIG._12

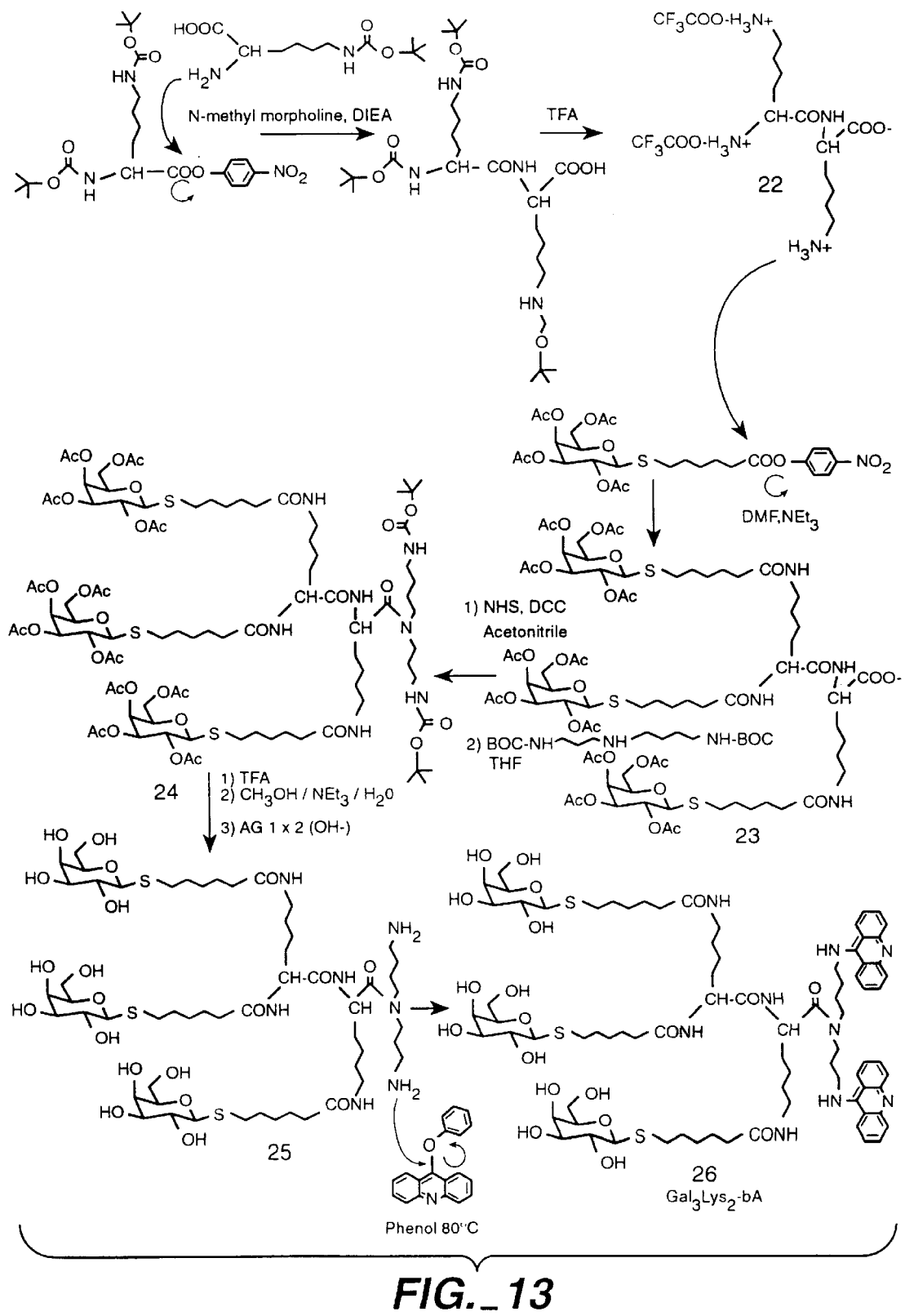
FIG._13

SELF-ASSEMBLING POLYNUCLEOTIDE DELIVERY SYSTEM

CROSS-REFERENCE TO RELATED CASE

This is a continuation of appplication Ser. No. 07/913,669 filed on Jul. 14, 1992, entitled SELF-ASSEMBLING POLYNUCLEOTIDE DELIVERY SYSTEM now abandoned which is a continuation-in-part of U.S. Ser. No. 07/864,876, filed Apr. 3, 1992, now abandoned.

TECHNICAL FIELD

This invention is in the field of oligonucleotide delivery and gene therapy. In particular this invention is directed to a self-assembling polynucleotide delivery system comprising components aiding in the delivery of the polynucleotide to the desired address which are associated via noncovalent interactions with the polynucleotide. The components of this system include DNA-masking components, cell recognition components, charge-neutralization and membrane-permeabilization components, and subcellular localization components.

BACKGROUND ART

Cystic Fibrosis (CF) is a fatal recessive genetic disease characterized by abnormalities in chloride transport (McPherson & Dorner, 1991). The locus of the disease has been traced to mutations in the gene encoding the cystic fibrosis transmembrane conductance regulator (CFTR). J. R. Riordan et al., *Science* (1989) 245:1066–1073; B. Kerem et al., *Science* (1989) 245:1073–1080. Correction of the underlying gene defect by complementation or replacement of the defective CFTR is the ultimate cure for CF. Gene therapy, the in vivo delivery and expression of genes, is a fast-developing science that can be used to replace defective genes.

Gene therapy is already feasible. T. Friedmann, *Science* (1989) 244:1275–1281; M. Bluestone, *Biotechnol* (1992) 10:132–134. Systems and polymers for delivery of polynucleotides are known in the art. P. L. Felgner, *Adv Drug Delivery Rev* (1990) 5:163–187. Adenoviral vectors have been used to transfer CFTR to the cotton rat lung in vivo. M. A. Rosenfeld et al., *Cell* (1992) 68:143–155. Although high levels of transfection in vivo have been reported with the adenoviral vectors, non-viral delivery systems have a number of advantages and should be vigorously developed. Rosenfeld et al., supra; M. A. Rosenfeld et al., *Science* (1991) 252:431–434.

During the past decade, a number of methods have been developed to introduce functional genes into mammalian cells in vitro. These techniques are applicable to gene therapy if the target cells can be removed from the body, treated, and the transfected cells amplified and then returned to the patient. This option is not possible for CF patients. At present the best in vivo transfection efficiencies are obtained with retroviruses (Bluestone, supra) and adenoviruses (Rosenfeld et al., supra). However the efficiency is variable and a concern is that virus based gene delivery might cause viral infection or cancer. Initial human clinical trials have revealed no acute complications of retroviral vectors but the possibility of long-term complications mandate careful patient monitoring. K. Cornetta et al., *Human Gene Ther* (1991) 2:3–14.

The risks of using viral based vectors and the conceptual advantages in using plasmid DNA constructs for gene therapy (discussed in P. L. Felgner et al., *Nature* (1991) 349:351–352) have led to a parallel development of various physical and chemical methods for gene transfer. The most intensely studied systems involve treatment of the cells with calcium phosphate or a cationic facilitator (Felgner et al., supra). Other popular methods involve DNA injection during physical puncture of the membrane (M. R. Capecchi, *Cell* (1980) 22:479–485) or passive uptake during permeabilization or abrasion of the cellular membrane (Felgner et al., supra). Each method is intrinsically aggressive and applicable only in vitro.

This invention is in the field of direct gene delivery that does not involve the use of viral vehicles. A non-viral carrier for gene delivery must be able to surmount many barriers: it must survive in circulation, it must be able to target the cell of choice, it must be able to introduce DNA into the cytoplasm, and it must be able to transport the DNA into the nucleus.

Masking. One concern about the direct delivery of genes in vivo is the ability of the polynucleotide to survive in circulation long enough to arrive at the desired cellular destination. "Masking", or protecting the polynucleotides is one way to address this concern.

Microparticulates (such as the erythrocyte ghost, reconstituted viral envelopes and liposomes) have been used in part as protection in gene transfer. C. Nicolau et al., *Crit Rev Ther Drug Carr Sys* (1989) 6:239–271; R. J. Mannio et al., *Biotechniques* (1988) 6:682–690. The most successful liposome system uses the cationic lipid reagent N-[1(-2,3-dioleoyloxy)propyl]-N,N,N-trimethylammonium chloride (DOTMA). P. L. Felgner et al., *Proc Natl Acad Sci (USA)* (1987) 84:7413–7417. DOTMA is mixed with phosphatidylethanolamine (PE) to form the reagent Lipofectin™. The advantage of using Lipofectin™ is that the cationic liposome is simply mixed with the DNA and added to the cell. It is not necessary to encapsulate the DNA inside of the liposome with the cationic reagents. Lipofectin™ has been used to transfect reporter genes into human lung epithelial cells in culture (L. Lu et al., *Pflugers Arch* (1989) 415:198–203), to introduce the CAT gene into rats by intratracheal route (T. A. Hazinski et al., *Am J Respir Cell Mol Biol* (1991) 4:206–209) and to introduce the CAT gene into mice by the intratracheal and intravenous route (K. L. Brigham et al., *Am J Med Sci* (1989) 298:278–281; A. Bout et al., "Abstracts of the 1991 Cystic Fibrosis Conference", Abstract no. 87 (1991)). About 50% of the airway epithelial cells transiently expressed the β galactosidase reporter gene (Hazinski et al., supra) but the level of expression was not quantitated. When chloramphenicol acetyltransferase (CAT) attached to a steroid sensitive promoter was transfected into rat lung, expression could be positively regulated by dexamethasone. Hazinski et al., supra. Cytotoxicity is a problem with high concentrations of Lipofectin™.

Substitutes for DOTMA include lipopolyamine (J. Loeffler et al., *J Neurochem* (1990) 54:1812–1815), lipophilic polylysines (X. Zhou et al., *Biochim Biophys Acta* (1991) 1065:8–14) and a cationic cholesterol (X. Gao et al., *Biochem Biophys Res Comm* (1991) 179:280–285). These have been used to mediate gene transfer in culture. Although there is some improvement over transfection rates observed with Lipofectin™ (about threefold), toxicity remains a problem. Studies on the mechanism responsible for transfection using the cationic lipids have been notably lacking. The past approach has been to synthesize different cationic lipids and try them in transfection assays, rather than to systematically study how the delivery systems introduce DNA into the cell. DOTMA/PE liposomes can undergo bilayer fusion with anionic liposomes (N. Duzgunes et al., *Biochem* (1989)

28:9179–9184) which suggests that direct entry of the DNA via the plasma membrane is involved with DOTMA's mode of action. High efficiency transfection using cationic lipids systems requires the inclusion of PE, possibly because PE can form intramembrane lipid intermediates which facilitate membrane fusion. The role of PE in membrane permeabilization and fusion has been extensively studied. E.g., M.-Z. Lai et al., *Biochem* (1985) 24:1646–1653; H. Ellens et al., *Biochem* (1986) 25:285–294; J. Bentz et al., *Biochem* (1987) 26:2105–2116).

Cellular Targeting. Efficient gene transfer requires targeting of the DNA to the cell of choice. Recently, procedures based upon receptor mediated endocytosis have been described for gene transfer. G. Y. Wu et al., *J Biol Chem* (1987) 262:4429; G. Y. Wu et al., *J Biol Chem* (1988) 263:14621–14624. A cell-specific ligand-polylysine complex is bound to nucleic acids through charge interactions. The resulting complex is taken up by the target cells. Wu et al., supra, reported efficient transfection of the human hepatoma cell line HepG2 and of rat hepatocytes in vivo using this delivery system with asialoorosomucoid as a ligand. Huckett et al., *Biochem Pharmacol* (1990) 40:253–263, reported stable expression of an enzymatic activity in HepG2 cells following insulin-directed targeting. Finally Wagner et al., *Proc Natl Acad Sci* (*USA*) (1990) 87:3410–3414 and (1991) 88:4255–4259 observed transferrin-polycation-mediated delivery of a plasmid into the human leukemic cell line K-562 and subsequent expression of the encoded luciferase gene. However, the described delivery systems are based upon high molecular weight targeting proteins linked to DNA through a polylysine linker. These large ligand-polycation conjugates are heterogenous in size and composition, not chemically well-defined, and difficult to prepare in a reproducible fashion (Wu et al., supra; Wagner et al., supra). Moreover, in many of the receptor mediated systems, chloroquine or other disruptors of intracellular trafficking are required for high levels of transfection. In one study, adenovirus has been used to enhance gene delivery of the receptor mediated systems. D. T. Curiel et al., *Proc Natl Acad Sci* (*USA*) (1991) 88:8850–8854.

Together these studies show that genes can be delivered into the interior of mammalian cells by receptor mediated endocytosis and a fraction of the exogenous DNA escapes degradation, enters the nucleus, and is expressed. The level of expression is low, probably due to the limited entry of the foreign DNA into the cytoplasm.

Charge Neutralization and Membrane Permeabilization. Direct delivery of genes is aided by the ability to neutralize the large negative charge on the polynucleotide, and the (often concomitant) ability to permeabilize the membrane of the targeted cell. The use of polycations to neutralize the polynucleotide charge and aid in the membrane permeabilization and translocation is well known. Felgner, supra. Cationic lipids have also been used for this purpose. P. L. Felgner et al., *Proc Natl Acad Sci* (*USA*) (1987) 84:7413–7417; U.S. Pat. No. 4,946,787 to Eppstein et al. Certain cationic lipids termed lipopolyamines and lipointercalants are also known. J.-P. Behr, *Tet Lett* (1986) 27:5861–5864.

Subcellular Localization. Once the polynucleotide has entered the targeted cell, direct delivery of genes would be aided by the ability to direct the genes to the proper subcellular location. One obvious target for the delivery of deoxyribonucleotides is the nucleus. Ligands known to aid in this process are nuclear localization peptides, or proteins containing these nuclear localization sequences. C. Dingwall et al., *TIBS* (1991) 16:478–481.

Y. Kaneda et al., *Science* (1989) 243:375–378, showed that the transfection efficiency obtained with reconstituted viral envelopes is increased when the foreign gene is co-delivered into the target cells with nuclear proteins. DNA mixed with nuclear proteins exhibit a modest increase in transfection over DNA that was mixed with albumin (Kaneda et al.). The assumption is that the DNA is incorporated into the nucleus more readily when proteins containing the nuclear localization sequence (NLS) SEQ ID NO:1 (P. A. Silver, *Cell* (1991) 64:489–497) are associated with the plasmid. The NLS on a protein designates it for transport through the nuclear pore. Nuclear localization sequences of 14 amino acids have been attached to a variety of macromolecules and even gold particles (150 A diameter) and, when introduced into the cytoplasm, they are rapidly incorporated into the nucleus (D. R. Findlay et al., *J Cell Sci Supp* (1989) 11:225–242; Silver, supra). The suggestion that nuclear entry is rate limiting for successful, stable transfection is also supported by the finding that plasmid DNA microinjected into the cytoplasm is unable to bring about transfection of cells (no transfection out of 1000 cytoplasmic injections, whereas microinjection of plasmids directly into the nucleus results in transfection in greater than 50% of the microinjected cells. Cappechi, supra. If the attachment of nuclear localization signals on the plasmid leads to transport of plasmid DNA into the nucleus, the transfection efficiency should increase. We propose a novel method to attach NLS and other ligands to the desired polynucleotide.

Finally, investigators have demonstrated that transfection efficiencies increase when DNA is condensed using various cationic proteins. T. I. Tikchonenko et al., *Gene* (1988) 63:321–330; M. Bottger et al., *Biochim Biophys Acta* (1988) 950:221–228; Wagner et al., supra. The reason why DNA condensation increases transfection is not readily apparent, it may increase cellular uptake of DNA (Wagner et al., supra) but it also can decrease susceptibility of the DNA to nuclease activity which may result in higher amounts of intact DNA in the cell.

Polynucleotide Association. Direct delivery of genes associated with one of the above-discussed classes of molecules, is further aided by the ability of those components to remain associated with the DNA. Wu et al., supra, associated their receptor ligand with the polynucleotide by covalently attaching the ligand to the polycation polylysine. Wagner et al., *Bioconjugate Chem.* (1991) 2:226–231, in addition to polylysine, also covalently attached the ligand to a DNA intercalator, ethidium homodimer (5,5'-diazadecamethylenebis(3,8-diamino-6-phenylphenanthridium) dichloride dihydrochloride). P. E. Nielsen, *Eur J Biochem* (1982) 122:283–289, associated photoaffinity labels to DNA by covalent attachment to 9-aminoacridine and certain bis-acridines.

None of the above references describe a system for polynucleotide delivery aimed at multiple aspects of the problems involved in bringing a circulating polynucleotide to a targeted subcellular location of a targeted cell. This invention addresses those problems by associating the polynucleotide with a combination of one or more of the following functional components: DNA-masking components, cell recognition components, charge-neutralization and membrane-permeabilization components, and subcellular localization components.

SUMMARY OF THE INVENTION

In light of the aforementioned problems of direct gene delivery, this invention contemplates a self-assembling polynucleotide delivery system utilizing a combination of one or more, preferably two or more of the following functional components: DNA-masking components, cell recognition components, charge-neutralization and membrane-permeabilization components, and subcellular localization components. Each component in this system is able to perform its indicated function and also be capable of assembling or disassembling with the polynucleotide as required. For example, certain components may have to dissociate from the polynucleotide in order for it to perform its desired function.

It is accordingly a primary object of this invention to provide a composition for presenting a polynucleotide to a subcellular component of a eukaryotic cell comprising the polynucleotide associated with a membrane-permeabilizing component capable of transporting the polynucleotide across the cytoplasmic membrane of the eukaryotic cell.

It is another object of this invention to provide a composition for presenting a polynucleotide to the nucleus of a eukaryotic cell comprising the polynucleotide associated with a cell recognition component capable of recognizing the eukaryotic cell.

It is yet another object of this invention to provide a composition for presenting a polynucleotide to the nucleus of a eukaryotic cell comprising the polynucleotide associated with both a cell recognition component capable of recognizing the eukaryotic cell, and a membrane-permeabilizing component capable of transporting the polynucleotide across the cytoplasmic membrane of the eukaryotic cell.

It is a further object of this invention to provide a composition for presenting a polynucleotide to a subcellular component of a eukaryotic cell comprising the polynucleotide associated with a subcellular-localization component capable of delivering the polynucleotide from the cytoplasm of the eukaryotic cell to a subcellular component of the eukaryotic cell.

It is still a further object of this invention to provide a composition for presenting a polynucleotide to a subcellular component of a eukaryotic cell comprising the polynucleotide, a cell recognition component capable of recognizing said eukaryotic cell, a membrane-permeabilizing component capable of transporting the polynucleotide across the cytoplasmic membrane of said eukaryotic cell, a subcellular-localization component capable of delivering the polynucleotide from the cytoplasm of said eukaryotic cell to a subcellular component of said eukaryotic cell, and a masking component capable of increasing the circulatory half-life of the polynucleotide.

It is another object of this invention to provide a component useful in self-assembling polynucleotide delivery systems having the formula

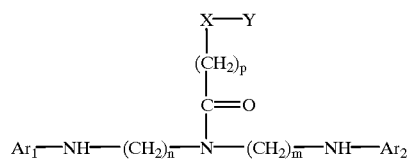

wherein each of n and m is independently an integer of 1 to 20, p is an integer of 0 to 20, $Ar_1$ and $Ar_2$ are independently selected from the group consisting of ethidium bromide, acridine, mitoxantrone, oxazolopyridocarbazole, ellipticine and N-methyl-2,7-diazapyrenium, and derivatives thereof, X is a reactive coupling group, and Y is selected from the group consisting of masking compound, cell surface receptor ligands, subcellular localization sequences, and membrane permeabilizing components.

It is still another object of this invention to provide a reactive intercalating component having the formula

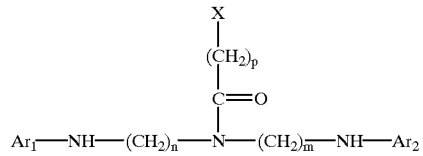

wherein each of n and m is independently an integer of 1 to 20, p is an integer of 0 to 20, $Ar_1$ and $Ar_2$ are independently selected from the group consisting of ethidium bromide, acridine, mitoxantrone, oxazolopyridocarbazole, ellipticine and N-methyl-2,7-diazapyrenium, and derivatives thereof, and X is a reactive group.

BRIEF DESCRIPTION OF THE FIGURES

FIG. 1 shows one embodiment of the polynucleotide delivery system of the invention, where NLS is a nuclear localization sequence, MD is a membran-permeabilization component, and Ligand is a cell recognition component.

FIG. 2 shows the structure of gramicidin S.

FIG. 3 compares the efficiency of luciferase transfection with Lipofectin™, pH-sensitive liposomes, and the gramicidin S/DOPE/DNA complex.

FIG. 4 shows the effect of gramicidin S to DNA ratio on transfection efficiency.

FIG. 5 shows the effect of gramicidin S to DOPE ratio on transfection efficiency.

FIG. 6 shows the effect of lipid type in the gramicidin S/lipid/DNA complex on transfection efficiency.

FIG. 7 shows the effect of substituting other peptides for gramicidin S in the gramicidin S/lipid/DNA complex on transfection efficiency.

FIG. 8 shows a synthetic scheme for attaching targeting carbohydrates and/or reactive maleimide to spermidine bis-acridine.

FIG. 9 shows the basic scheme for coupling eptides to the maleimido-spermidine bis-acridine.

FIG. 10 shows a synthetic scheme for coupling to a degradable Lys-Lys peptide bis-acridine.

FIG. 11 shows the results of the gel retardation assay of Example 3.

FIG. 12 shows the ability of several galactosyl bis-acridines to bring plasmid DNA into hepatocytes.

FIG. 13 shows a synthetic scheme for the trigalactosylated spermidine bis-acridine of Example 6.

DETAILED DESCRIPTION OF THE INVENTION

Definitions:

The term "polynucleotide" as used herein, includes RNA or DNA sequences of more than one nucleotide in either single chain, duplex or multiple chain form. "Polynucleotide" is generic to polydeoxyribonucleotides (containing 2'-deoxy-D-ribose or modified forms thereof), i.e., DNA, to polyribonucleotides (containing D-ribose or modified forms thereof), i.e., RNA, and to any other type of polynucleotide which is an N-glycoside or C-glycoside of a purine or pyrimidine base, or modified purine or pyrimidine base or abasic nucleotides. The polynucleotide may encode promoter regions, operator regions, structural regions, termination regions, combinations thereof or any other genetically relevant material.

The polynucleotides of the invention may also contain one or more "substitute" linkages as is generally understood in the art. Some of these substitute linkages are non-polar and contribute to the desired ability of the polynucleotide to diffuse across membranes. Others contribute to the increased or decreased biodegradability of the polynucleotide. (Biodegradability will be affected, for example, by increased or decreased nuclease sensitivity.) These "substitute" linkages are defined herein as conventional alternative linkages such as phosphorothioate or phosphoramidate, are synthesized as described in the generally available literature. Not all such linkages in the same polynucleotide need be identical.

Modifications in the sugar moiety of the polynucleotide, for example, wherein one or more of the hydroxyl groups are replaced with halogen, aliphatic groups, or functionalized as ethers, amines, and the like, or wherein the ribose or deoxyribose is replaced with other functionally equivalent structures, are also included. Modifications in the base moiety include alkylated purines or pyrimidines, acylated purines or pyrimidines, or other heterocycles. Such "analogous purines" and "analogous pyrimidines" are those generally known in the art, many of which are used as chemotherapeutic agents.

In particular, the sugar-phosphate backbone of the polynucleotide may be replaced with a non-carbohydrate backbone such as a peptide or other type of polymer backbone as discussed in P. E. Nielsen et al., *Science* (1991) 254:1497–1500.

The term "functional component" as used herein, includes DNA-masking components, cell recognition components, charge-neutralization and membrane-permeabilization components, and subcellular-localization components.

The term "DNA-masking component", as used herein, refers to a molecule capable of masking all or part of the polynucleotide, thereby increasing its circulatory half-life by inhibiting attack by degrading reagents (such as nucleases) present in circulation.

The term "membrane-permeabilizing component", as used herein, refers to any component that aids in the passage of a polynucleotide across a membrane. Thus, this term encompasses in part charge-neutralizing components, usually polycations, that neutralize the large negative charge on polynucleotides, and enable the polynucleotide to transverse the hydrophobic interior of a membrane. Many charge-neutralizing components can act as membrane-permeabilizers. Membrane-permeabilization may also arise from amphipathic molecules.

A membrane permeabilizer is a molecule that can assist a normally impermeable molecule to traverse cellular membranes and gain entrance to the cytoplasm of the cell. A membrane permeabilizer may be a peptide, bile salt, glycolipid, carbohydrate, phospholipid or detergent molecule. Membrane permeabilizers often have amphipathic properties such that one portion is hydrophobic and another is hydrophilic, permitting them to interact with membranes.

The term "liposome" as used herein, refers to small vesicles composed of amphipathic lipids arranged in spherical bilayers. Liposomes are usually classified as small unilamellar vesicles (SUV), large unilamellar vesicles (LUV), or multi-lamellar vesicles (MLV). SUVs and LUVs, by definition, have only one bilayer, whereas MLVs contain many concentric bilayers. Liposomes may be used to encapsulate various materials, by trapping hydrophilic molecules in the aqueous interior or between bilayers, or by trapping hydrophobic molecules within the bilayer.

Liposomes exhibit a wide variety of characteristics, depending upon their size, composition, and charge. For example, liposomes having a small percentage of unsaturated lipids tend to be slightly more permeable, while liposomes incorporating cholesterol or other sterols tend to be more rigid and less permeable. Liposomes may be positive, negative, or neutral in charge, depending on the hydrophilic group. For example, choline-based lipids impart an overall neutral charge, phosphate and sulfate based lipids contribute a negative charge, glycerol-based lipids are generally negatively-charged, and sterols are generally neutral in solution but have charged groups.

The term "cell recognition component" as used herein, refers to a molecule capable of recognizing a component on the surface of a targeted cell. Cell recognition components include: antibodies to cell surface antigens, ligands for cell surface receptors including those involved in receptor-mediated endocytosis, peptide hormones, and the like.

The term "DNA-associating moiety" refers to a molecule or portions thereof that interacts in a noncovalent fashion with nucleic acids. DNA-associating moieties include major- and minor-groove binders, which are molecules thought to interact with DNA by associating with the major or minor groove of double-stranded DNA. DNA associating moieties also include DNA intercalators, which are planar molecules or planar portions of molecules thought to intercalate into DNA by inserting between and parallel to nucleotide base pairs. DNA associating moieties further include polycations, thought to associate with the negative charges on the DNA backbone. When a single-stranded DNA or RNA is used as the therapeutic strand, the complementary "linker strand" as described herein may functionally act as the "DNA-associating moiety".

DNA associating moieties may be covalently linked through a "reactive group" to a functional component of this invention. These reactive groups are easily reacted with a nucleophile on the functional component. Such reactive groups (with their corresponding reactive nucleophiles) include, but are not limited to: N-hydroxysuccinimide (amine), maleimide and maleimidophenyl (sulfhydryl), pyridyl disulfide (sulfhydryl), hydrazide (carbohydrate), and phenylglyoxal (arginine).

The term "subcellular-localization component" as used herein, refers to a molecule capable of recognizing a subcellular component in a targeted cell. Recognized subcellular components include the nucleus, ribosomes, mitochondria, and chloroplasts. Particular subcellular-localization components include the "nuclear-localization components" that aid in bringing molecules into the nucleus and are known to include the nuclear localization peptides and amino acid sequences.

The Compositions:

The compositions of this invention in part are self-assembling polynucleotide delivery systems utilizing a polynucleotide in combination with one or more, preferably two or more of the following functional components: DNA-masking components, cell recognition components, charge-neutralization and membrane-permeabilization components, and subcellular localization components. Each element in this system is able to perform its indicated function and also be capable of assembling or disassembling with the polynucleotide as required. Individual elements of this system, and methods and intermediates for making these elements are also contemplated as part of this invention. One embodiment of the system is shown in FIG. 1.

The Polynucleotide

The polynucleotide may be single-stranded DNA or RNA, or double-stranded DNA or DNA-RNA hybrid. Triple- or quadruple-stranded polynucleotides with therapeutic value are also contemplated to be within the scope of this invention. Examples of double-stranded DNA would include structural genes, genes including operator control and termination regions, and self-replicating systems such as plasmid DNA.

Single-stranded polynucleotides include antisense polynucleotides (DNA and RNA), ribozymes and triplex-forming oligonucleotides. This "therapeutic strand", in order to have prolonged activity, preferably has as some or all of the nucleotide linkages stable, non-phosphodiester linkages. Such linkages include, for example, the phosphorothioate, phosphorodithioate, phosphoroselenate, or O-alkyl phosphotriester linkages wherein the alkyl group is methyl or ethyl.

For these single-stranded polynucleotides, it may be preferable to prepare the complementary strand to the therapeutic strand as part of the administered composition. This complementary strand is designated the "linker strand", and is usually synthesized with a phosphodiester linkage so that it is degraded after entering the cell. The "linker strand" may be a separate strand, or it may be covalently attached to or a mere extension of the therapeutic strand so that the therapeutic strand essentially doubles back and hybridizes to itself.

The linker strand may also have functionalities on the 3' or 5' end or on the carbohydrate or backbone of the linker that serve as functional components to enhance the activity of the therapeutic strand. For example, the phosphodiester linker strand may contain a targeting ligand such as a folate derivative that permits recognition and internalization into the target cells. If the linker is attached to its complementary therapeutic strand that is composed of degradation-resistant linkages, the duplex would be internalized. Once inside the cell, the linker would be degraded, releasing the therapeutic strand. In this manner the therapeutic strand would have no additional functionalities attached and its function would not be impeded by non-essential moieties. This strategy could be applied to any antisense, ribozyme or triplex-forming polynucleotide. It would be used to deliver antiviral, antibacterial, antineoplastic, antiinflammatory, antiproliferative, anti-receptor blocking or anti-transport polynucleotides and the like.

A separate "linker strand" may be synthesized to have the direct complementary sequence to the therapeutic strand and hybridize in a one-on-one fashion. Alternatively, the linker strand may be constructed so that the 5' region of the linker strand hybridizes to the 5' region of the therapeutic strand, and the 3' region of the linker strand hybridizes to the 3' region of the therapeutic strand to form a concatenate of the following structure

This concatenate has the advantage that the apparent molecular weight of the therapeutic nucleic acids is increased and its pharmacokinetic properties and targeting ligand:therapeutic oligonucleotide ratio can be adjusted to achieve the optimal therapeutic effect.

The Functional Components

DNA-Masking Components. The DNA-masking element of this system is a molecule capable of masking all or part of the polynucleotide, thereby increasing its circulatory half-life by inhibiting attack by degrading reagents present in circulation.

In this invention, polyethylene glycol (PEG) can be covalently linked with a DNA-associating moiety by conventional methods as described below, and used as a DNA-masking component. The PEG will have a molecular weight from about 700 to about 20,000 Daltons, preferably about 1800 to 6000 daltons, and is preferably present in a ratio (molecules PEG:bp DNA) from about 1:4 to 1:100, more preferably about 1:20.

Alternatively, DNA may be masked through association with lipids. In one embodiment, the DNA is encased in standard liposomes as described, for example, in U.S. Patent No. 4,394,448 to Szoka et al., the specification of which is hereby incorporated by reference. In another embodiment, the DNA is incubated with a synthetic cationic lipid similar to those described in U.S. Pat. No. 4,897,355 to Eppstein et al. These cationic lipids have the general formula

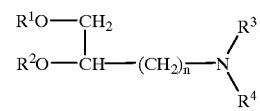

wherein n is an integer from 1 to 8, $R^1$ and $R^2$ are the same or different and are alkyl or alkenyl having from 6 to 24 carbon atoms, $R^3$ is hydrogen, alkyl or alkylamine having from 1 to 10 carbon atoms, and $R^4$ is a positively charged linear or branched alkyl or alkylamine having from 1 to 30 carbon atoms, wherein one or more of the carbon atoms may be substituted with NR', wherein R' is hydrogen, alkyl or alkylamine having from 1 to 10 carbons. Preferred groups that can function as the —N—R' moiety are tris(aminoethyl) amine $(NH_2CH_2CH_2)_3N$, agmatine (decarboxyarginine) $H_2N(CH_2)_4C(=NH)NH_2$, 3-aminoethyl-1,3-propanediamine $H_2N(CH_2)_3NH(CH_2)_2NH_2$, 3-dimethylaminopropylamine $(CH_3)_2NH(CH_2)_3NH_2$, iminobis(N,N')dimethylpropylamine $NH((CH_2)_3N(CH_3)_2)_2$, iminobis(3-aminopropyl)-1,3-propanediamine, 1,4-bis(3-aminopropyl)piperazine, bis(propylamine) $(NH_2(CH_2)_3)_2NH$, spermidine, and spermine, wherein these groups are attached to the lipid molecule through one of their nitrogen atoms.

In a specifically preferred embodiment, the synthetic cationic lipid is a synthetic cationic tail lipid having the formula

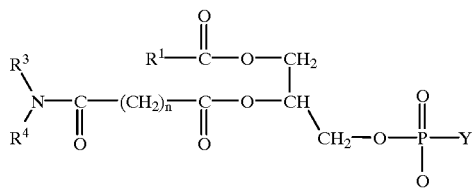

wherein n is an integer from 6 to 24, Y is selected from the group consisting of hydrogen, ethanolamine, choline, glycerol, serine and inositol, $R^1$ is alkyl or alkenyl having from 6 to 24 carbon atoms, $R^3$ is hydrogen, alkyl or alkylamine having from 1 to 10 carbon atoms, and $R^4$ is a positively charged linear or branched alkyl or alkylamine having from 1 to 30 carbon atoms, wherein one or more of the carbon atoms may be substituted with NR', wherein R' is hydrogen, alkyl or alkylamine having from 1 to 10 carbons. Preferred groups that can function as the —N—R' moiety are tris(aminoethyl)amine (NH$_2$CH$_2$CH$_2$)$_3$N, agmatine (decarboxyarginine) H$_2$N(CH$_2$)$_4$C(=NH)NH$_2$, 3-aminoethyl-1,3-propanediamine H$_2$N(CH$_2$)$_3$NH(CH$_2$)$_2$NH$_2$, 3-dimethylaminopropylamine (CH$_3$)$_2$NH(CH$_2$)$_3$NH$_2$, iminobis(N,N')dimethylpropylamine NH((CH$_2$)$_3$N(CH$_3$)$_2$)$_2$, iminobis(3-aminopropyl)-1,3-propanediamine, 1,4-bis(3-aminopropyl)piperazine, bis(propylamine) (NH$_2$(CH$_2$)$_3$)$_2$NH, spermidine, and spermine, wherein these groups are attached to the lipid molecule through one of their nitrogen atoms.

It has been found that the above-described synthetic cationic lipids effectively mask the DNA when associated therewith. Without attempting to limit the invention in any way, it is believed that the lipids form a monolayer structure that encapsulates the DNA in some fashion.

Cell Recognition Components. The cell recognition element of this system is a molecule capable of recognizing a component on the surface of a targeted cell, covalently linked with a DNA-associating moiety by conventional methods as described below. Cell recognition components include: antibodies to cell surface antigens, ligands for cell surface receptors including those involved in receptor-mediated endocytosis, peptide hormones, etc. Specific ligands contemplated by this invention include: carbohydrate ligands such as galactose, mannose, mannosyl 5-phosphate, fucose, sialic groups, N-acetylglucosamine or combinations of these groups as complex carbohydrates such as those found on glycolipids of the blood groups or on various secreted proteins. Other ligands include folate, biotin, various peptides that can interact with cell surface or intracellular receptors such as the chemoattractant peptide SEQ ID NO:2, peptides containing the arg-asp-glycine sequence or SEQ ID NO:3 peptides, peptides that contain a cystine residue or that interact with cell surface protein such as the human immunodeficiency virus GP-120, and peptides that interact with CD-4. Other ligands include antibodies or antibody fragments such as described by A. Hertler and A. Frankel, *J Clin Oncol* 7: 1932–1942. The specificity of the antibodies can be directed against a variety of epitopes that can be expressed on cell surfaces including histocompatability macromolecules, autoimmune antigens, viral, parasitic or bacterial proteins. Other protein ligands include hormones such as growth hormone and insulin or protein growth factors such as GM-CSF, G-CSF, erythropoietin, epidermal growth factor, basic and acidic fibroblast growth factor and the like. Other protein ligands would include various cytokines that work through cell surface receptors such as interleukin 2, interleukin 1, tumor necrosis factor and suitable peptide fragments from such macromolecules.

Membrane-Permeabilizing Components. The membrane-permeabilizing element of this system is a molecule that aids in the passage of a polynucleotide across a membrane. The liposomes and synthetic cationic lipids described above as DNA-masking components also may function as membrane-permeabilization components.

The membrane-permeabilizing components of this invention also include polycations that neutralize the large negative charge on polynucleotides. Polycations of this invention include polylysine, polyarginine, poly (lysine-arginine) and similar polypeptides, and the polyamines and the polycationic dendrimers. D. A. Tomalia et al., *Agnew. Chem. Int. Ed. Engl.* (1990) 29:138–175. Another class of polycations are the cationic bile salts having the following formula:

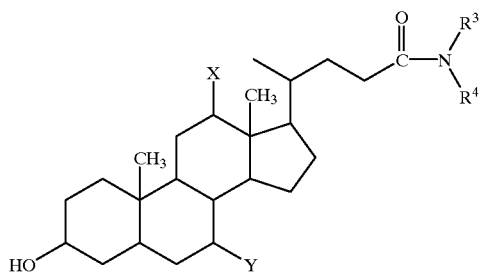

wherein X and Y are independently H or OH, R$^3$ is hydrogen, alkyl or alkylamine having from 1 to 10 carbon atoms, and R$^4$ is a positively charged linear or branched alkyl or alkylamine having from 1 to 30 carbon atoms, wherein one or more of the carbon atoms may be substituted with NR', wherein R' is hydrogen, alkyl or alkylamine having from 1 to 10 carbons. Preferred groups that can function as the —N—R' moiety are tris(aminoethyl)amine (NH$_2$CH$_2$CH$_2$)$_3$N, agmatine (decarboxyarginine) H$_2$N(CH$_2$)$_4$C(=NH)NH$_2$, 3-aminoethyl-1,3-propanediamine H$_2$N(CH$_2$)$_3$NH(CH$_2$)$_2$NH$_2$, 3-dimethylaminopropylamine (CH$_3$)$_2$NH(CH$_2$)$_3$NH$_2$, iminobis(N,N') dimethylpropylamine NH((CH$_2$)$_3$N(CH$_3$)$_2$)$_2$, iminobis(3-aminopropyl)-1,3-propanediamine, 1,4-bis(3-aminopropyl) piperazine, bis(propylamine) (NH$_2$(CH$_2$)$_3$)$_2$NH, spermidine, and spermine, wherein these groups are attached to the bile salt through one of their nitrogen atoms.

In a different embodiment, the membrane-permeabilizing component of the invention is an amphipathic cationic peptide. Amphipathic cationic peptides are peptides whose native configuration is such that the peptide is considered to have a cationic face and a neutral, hydrophobic face. In a preferred embodiment, the peptide is a cyclic peptide. Examples of the amphipathic cationic cyclic peptides of this invention are gramicidin S (the structure of which is shown in FIG. 2), and the tyrocidines. The peptide may also contain some or all of the amino acids in the D configuration as opposed to the naturally occurring L configuration.

In a particularly preferred embodiment, the membrane-permeabilizing element includes, in addition to the amphipathic cationic cyclic peptides, either (1) a lipid, or (2) a simple polyamine, or both.

The lipid of the invention is an amphipathic molecule which is capable of liposome formation, and is substantially non-toxic when administered at the necessary concentrations either in native form or as liposomes. Suitable lipids generally have a polar or hydrophilic end, and a non-polar or hydrophobic end. Suitable lipids include without limitation egg phosphatidylcholine (EPC), phosphatidylethanolamine, dipalmitoylphosphatidylcholine (DPPC), cholesterol (Chol), cholesterylphosphorylcholine, 3,6,9-tri-oxaoctan-1-ol-cholesteryl-3-ol, dimyristoylphosphatidylcholine (DMPC), and other hydroxy-cholesterol or aminocholesterol derivatives (see, e.g., K. R. Patel et al., *Biochim Biophys Acta* (1985) 814:256–64). The lipid is preferably added in the form of liposomes.

The added polyamine is preferably spermine or spermidine.

The membrane permeabilizing elements—the cyclic peptide and optional phospholipid and polyamine—may be added to the composition simultaneously or consecutively. Preferably, the cyclic peptide is added first, and the phospholipid or polyamine added later. The molar ratio of added cyclic peptide to added polyamine is preferably from about 1:1 to about 1:3. The molar ratio of added cyclic peptide to added phospholipid is preferably from about 1:1 to about 1:20.

Subcellular-Localization Components. The subcellular-localization element of this system is a molecule capable of recognizing a subcellular component in a targeted cell, covalently linked with a DNA-associating moiety by conventional methods as described below. Particular subcellular components include the nucleus, ribosomes, mitochondria, and chloroplasts.

In a preferred embodiment of this invention, the subcellular-localization component is a nuclear-localization component. The nuclear-localization components include known peptides of defined amino acid sequences, and longer sequences containing these peptides. One known peptide sequence is the SV 40 large T antigen heptapeptide SEQ ID NO:1. Other peptides include the influenza virus nucleoprotein decapeptide SEQ ID NO:4, and the adenovirus E1a protein sequence SEQ ID NO:5. Other sequences may be discerned from C. Dingwall et al., *TIBS* (1991) 16:478–481.

In another embodiment, the subcellular-localization component is a lysosomal-localization component. A known component for targeting the lysosome is a peptide containing the sequence SEQ ID NO:6. In yet another embodiment, the subcellular-localization component is a mitochondrial-localization component. A known component for targeting mitochondria is a peptide containing the sequence SEQ ID NO: 7.

DNA-Associating Moieties

The DNA-associating moiety of this system refers to a portion of a functional component that interacts in a non-covalent fashion with nucleic acids. The moiety is covalently linked to the rest of the functional component by conventional means or as described below. DNA-associating moieties are preferably major- and minor-groove binders, DNA intercalators, or general DNA binders. In the case of single-stranded polynucleotides, the DNA-associating moiety may even be the linker strand as described above. In such a case the functional moiety, such as the cell-recognition or subcellular-localization component is covalently linked to the linker strand.

In one preferred embodiment, the DNA-associating moiety is a major- or minor-groove binder. The major- and minor-groove binders are moieties known to associate or "lay in" the major or minor groove of DNA. These binders include distamycin A and Hoechst dye 33258.

In another embodiment, the DNA-associating moiety is a nonspecific DNA binder such as a polycation. Polycations of this invention include polylysine, polyarginine, poly (lysine-arginine) and similar polypeptides, and the polyamines and the polycationic dendrimers.

In another preferred embodiment, the DNA-associating moiety is a DNA intercalator. DNA intercalators are planar polycyclic molecules such as ethidium bromide, acridine, mitoxantrone, oxazolopyridocarbazole, ellipticine and N-methyl-2,7-diazapyrenium, and derivatives thereof. In a particular preferred embodiment, the intercalator is a dimer consisting of two covalently linked planar polycyclic molecules. A planar polycyclic dimer moiety of this invention has the structure

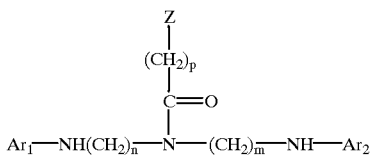

wherein Z is a bond;

wherein each of n and m is independently an integer of 1 to 20, p is an integer of 0 to 20, $Ar_1$ and $Ar_2$ are independently selected from the group consisting of ethidium bromide, acridine, mitoxantrone, oxazolopyridocarbazole, ellipticine and N-methyl-2,7-diazapyrenium, and derivatives thereof.

The values of n and m are important as they determine the spacing of the intercalated acridine monomers in the DNA. More preferred values of n and m are 3 and 4, respectively. Bis-acridine dimers, wherein $Ar_1$ and $Ar_2$ are both acridine, are preferred.

This preferred DNA-associating moiety will be covalently attached to a functional moiety, said moiety being a cell recognition moiety, subcellular localization moiety, or membrane permeabilizing moiety as described above. The value of p determines the separation of the intercalator from the functional moiety. Preferred values for p are from 0 to 8.

The DNA-associating moiety may be covalently attached to multiple copies of, or more than one functional moiety. For example, the bis-acridine dimer may be attached to three galactose residues that bind to the hepatocyte asialoorosomucoid receptor (See Compound 26 in FIG. 13).

A preferred method for attaching the DNA-associating dimer to the functional moiety involves a precursor having the formula

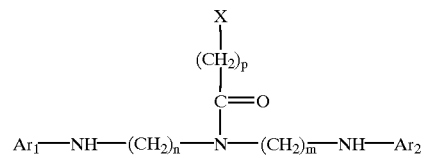

wherein each of n and m is independently an integer of 1 to 20, p is an integer of 0 to 20, $Ar_1$ and $Ar_2$ are independently selected from the group consisting of ethidium bromide, acridine, mitoxantrone, oxazolopyridocarbazole, ellipticine and N-methyl-2,7-diazapyrenium, and derivatives thereof; and X is a reactive group selected from the group consisting of N-hydroxysuccinimide, maleimide, maleimidophenyl, pyridyl disulfide., hydrazide, and phenylglyoxal.

In a preferred embodiment, $Ar_1$ and $Ar_2$ are acridine, p is 3 and X is p-maleimidophenyl. This intercalating moiety is then coupled to the functional moiety through a sulfhydryl group on the functional moiety, for example, to obtain a bifunctional component having the structure

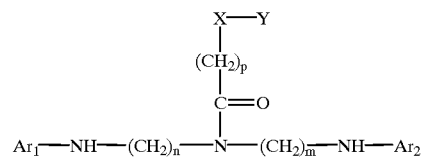

wherein

Y is a functional component;

each of n and m is independently an integer of 1 to 20, p is an integer of 0 to 20, $Ar_1$ and $Ar_2$ are independently selected from the group consisting of ethidium bromide, acridine, mitoxantrone, oxazolopyridocarbazole, ellipticine and N-methyl-2,7-diazapyrenium, and derivatives thereof; and X is a reactive group selected from the group consisting of N-hydroxysuccinimide, maleimide, maleimidophenyl, pyridyl disulfide, hydrazide, and phenylglyoxal.

Biodegradable linkers such as peptides having the sequence -lys-lys- may also be used in attaching the functional component to the intercalator.

In yet another embodiment of this invention, the planar polycyclic dimer has the formula

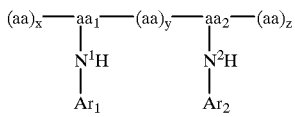

wherein $Ar_1$ and $Ar_2$ are independently selected from the group consisting of ethidium bromide, acridine, mitoxantrone, oxazolopyridocarbazole, ellipticine and N-methyl-2,7-diazapyrenium, and derivatives thereof;

each aa is independently an amino acid;

x and z are integers independently selected from 1 to 100;

y is an integer from 0 to 5;

$aa_1$ and $aa_2$ are lysine residues;

$N^1$ and $N^2$ are nitrogens from the $\epsilon$-amino groups of lysine residues $aa_1$ and $aa_2$.

Utility of the Polynucleotide Delivery System

The polynucleotide delivery system of the invention is useful in a therapeutic context. In therapeutic applications, the system of the invention can be formulated for a variety of modes of administration, including systemic and topical or localized administration. Techniques and formulations generally may be found in *Remington's Pharmaceutical Sciences*, Mack Publishing Co., Easton, Pa., latest edition.

For systemic administration, parenteral administration such as injection is preferred, including intramuscular, intravenous, intraperitoneal, and subcutaneous. For treating disorders of the lung, administration of the polynucleotide delivery system is done by inhalation or installation of the system directly into the lung.

For injection, the systems of the invention are formulated in liquid solutions, preferably in physiologically compatible buffers such as Hank's solution or Ringer's solution. In addition, the systems may be formulated in solid form and redissolved or suspended immediately prior to use. Lyophilized forms are also included.

Systemic administration can also be by transmucosal or transdermal means, or the systems can be administered orally, or through intranasal or inhaled aerosols. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the systems are formulated into conventional oral administration forms such as capsules, tablets, and tonics.

For topical administration, the systems of the invention are formulated into ointments, salves, gels, or creams, as is generally known in the art.

The following examples are meant to illustrate, but not to limit the invention.

EXAMPLE 1

Gramicidin S Transfection

Lipofectin™ is a synthetic cationic lipid, N-[1(-2,3-dioxeoyloxy)propyl]-N,N,N-trimethylammonium chloride, (DOTMA) in combination with phosphatidylethanolamine to form a charge complex with the negatively charged DNA. This complex is thought to fuse with the cell membrane and deliver DNA into the cytoplasm. An alternative approach uses pH sensitive liposomes composed of a negatively charged lipid and phosphatidylethanolamine. C. Y. Wang et al., *Biochem* (1989) 28:9508–9514. The delivery mechanism involves endocytosis of the liposome, as the pH in the endosome becomes acidic, the liposomal bilayer destabilizes and fuses with the endosomal membrane. The contents of the liposome are then introduced into the cytoplasm of the cell. C.-J. Chu et al., *Pharmaceut Res* (1990) 7:824–834.

We have compared Lipofectin™ to a pH-sensitive cholesterylhemisuccinate (Chems)/phosphatidylethanolamine (PE) liposome composition and to gramicidin S/dioleoylphosphatidylethanolamine (DOPE)/DNA complexes for the delivery and expression of DNA in mammalian cells. Plasmids containing strong promoters and either firefly luciferase or β galactosidase were used as indicators for gene transfer.

Cell Transfection Protocol.

CV-1, p388D1, HepG2 and HeLa cells were provided by the UCSF Cell Culture Facility. The Lipofectin™ reagent was used as described in the product insert (Gibco-BRL, Gaithersburg, Md.). KD83 cells were obtained from DNAX (Palo Alto, Calif.). Cells were plated at a density of 0.5–1× $10^6$ cells per 60 mm dish and grown 16 to 20 hrs at 37° C. under 5% $CO_2$ in appropriate media containing 10% fetal calf serum (FCS). Prior to incubation either with liposomes, Lipofectin™, or the gramicidin S/DOPE/DNA complex, cells were washed once with 2 ml of FCS-free DME H-21 medium. The transfection system was then added in 2 ml of the same media. In some experiments, transfection took place in 10% FCS containing DME H-21. After 5 hrs. media was removed and replaced by 3 ml of appropriate media with 10% FCS. Luciferase activity was measured after 48 hrs as described (A. R. Brasier et al., *Biotechniques* (1989) 7:1116–1122). Briefly, cells were washed twice with ice-cold phosphate buffer saline without $Ca^{2+}$ and $Mg^{2+}$ (PBS), treated with 400 μl of 25 mM glycylglycine (pH 7.8) in lysis buffer (containing 1% Triton) and scraped. After centrifugation, 100 μl of supernatant were mixed with an optimal amount of 50 mM ATP. D-luciferin (Sigma, 100 μl of a 1 mM solution) was then injected and the emitted light was integrated during the first 10 sec. using a bioluminometer (Bioluminescence Analytical Laboratories Inc., San Diego, Calif.). Proteins in the supernatant were assayed using the technique of Bradford (Bio-Rad kit). Results were expressed as light units per mg of cell-protein.

Luciferase Assay

In order to compare the potency of three different viral luciferase gene promoters, RSV, SV40 and CMV, we have transfected several mammalian cell lines with the corresponding Lipofectin™ complexed-plasmids. Each dish of cells received 2 μl of plasmid combined with 10 μl of Lipofectin™ as described above. Promoter strength was estimated by the luciferase expression at 48 hr given by the corresponding plasmid. The CMV promoter (pCLuc4 plasmid) led to the highest luciferase expression in HeLa, HepG2 and p388D1 cells, while SV40 promoter (pSV2 plasmid) was more potent in CV-1 cells. Therefore for further experiments, pSV2 plasmid has been used in CV-1 cells and pCLuc4 in other cell-lines.

Liposome characterization

Plasmid encapsulation efficiency was determined after separation of encapsulated from non-encapsulated plasmid on Ficoll gradients. About 22±3% of the total DNA added was encapsulated. Liposome diameters, measured by dynamic light scattering and were 372±38 nm, 295±65 nm and 464±20 nm for DOPE/CHEMS, DOPC/CHEMS and PS/Chol liposomes respectively (results are the mean±SD of three independent light scattering determinations).

A. Gramicidin S and Phosphatidylethanolamine

Typical complex preparation was made by diluting 20 μg of plasmid DNA in 300 μl of 30 mM Tris Cl pH 9 in a polystyrene tube. Gramicidin S was diluted in 30 mM pH 9 Tris Cl buffer to a concentration of 2 mg/ml from a stock solution at 20 mg/ml in DMSO. 20 μl of diluted gramicidin S (i.e. 40 μg) solution was added to the DNA and quickly mixed. Then 170 nmoles of liposomes were added slowly drop by drop to the DNA/gramicidin S mixture. Liposomes were prepared by drying 4 μmoles of lipids under nitrogen with a rotavapor and by rehydrating the film with 4 ml of 30 mM pH 9 Tris Cl buffer. Liposomes were subsequently sonicated 30 min under argon using a bath sonicator. The diameter of the complex was determined by dynamic light scattering. Other peptides including tyrocidine (U.S. Biochemicals), polymyxin B (Sigma) and polylysine 100 (Sigma) and the polycationic Starburst™ dendrimer (Polyscience, Inc.) were also used to form the complex with DNA and lipids.

The efficiency of transfection was monitored by measuring the expression of luciferase in Cv-1 cells as described above. The dose response comparing the amount of DNA added in the three transfection systems is illustrated in FIG. 3. Light units per mg cell protein in a log scale are plotted on the Y axis and the amount of DNA added on the X axis. The open boxes designate results using the Gramicidin S-dioleoylphosphatidyl ethanolamine-DNA complex. This complex induces a 10-fold greater level of expression than obtained with Lipofectin, and a 1000- to 10,000-fold greater level of expression than obtained using the pH sensitive liposomes.

B. Gramicidin S-DNA Ratio Effects

The gramicidin S-DOPE-DNA complex was prepared as described in Example 1-A except the amount of gramicidin S added to the complex was varied at constant amounts of DNA (20 ug) and DOPE (170 nmoles). The complex was added to CV-1 cells and the luciferase activity measured as described in Example 1. The result is presented in FIG. 4 and illustrates that maximum expression using the gramicidin S-DOPE-DNA complex occurs when the charge on the DNA is neutralized by the charge on the gramicidin.

C. Lipid Concentration Effects

The gramicidin S-DOPE-DNA complex was prepared as described in Example 1 except the amount of DOPE added to the complex was varied at constant amounts of DNA (20 ug) and gramicidin S (40 μg). The complex was added to CV-1 cells and the luciferase activity measured as described in Example 1. The result is presented in FIG. 5, which illustrates that in the absence of the DOPE, expression is low. Maximum expression using the gramicidin S-DOPE-DNA complex occurs when the ratio of DOPE to gramicidin S is above 5/1:mole/mole.

D. Lipid Type Effects

The gramicidin S-lipid-DNA complex was prepared as described in Example 1 except the type of phospholipid added to the complex was varied at constant amounts of DNA (20 ug) and gramicidin S(40 ug). The lipid compositions employed were DOPE; DOPE: dioleoylphosphatidylcholine (DOPC):2/1, palmitoyloleoylphosphatidylethanolamine (POPE), monomethyl DOPE (mmDOPE); dimethyl DOPE (dm DOPE); DOPC and dipalmitoylphosphatidylethanolamine (DPPE). The complex was added to CV-1 cells and the luciferase activity measured as described in Example 1. The result is presented in FIG. 6, which illustrates that expression of luciferase activity is maximal with DOPE or a mixture of DOPE/DOPC:2/1 in the complex. Luciferase activity is appreciably diminished when the amino group on the DOPE is substituted with 2 (dm DOPE) or 3 methyl groups (DOPC). Expression of the encoded gene is also appreciably reduced when DPPE is used. This latter lipid has saturated acyl chains and a high transition temperature, which means the acyl chains of DPPE are less fluid than the other lipids tested in this series.

E. Effects of Added Non-Amphipathic Positively Charged Spermidine

The data presented in Example 2 show that gene expression due to the gramicidin S-DOPE-DNA complex is maximal when the negative charges on DNA are neutralized by the positive charges on gramicidin. To determine whether charge neutralization or membrane permeabilization is more important for gene transfer using this system, the positive charge contribution from gramicidin S was incrementally replaced by the positively charged polyamine, spermidine. The gramicidin S-lipid-DNA complex was prepared as described in Example 1 except the amount of gramicidin S added to the complex was varied at constant amounts of DNA (20 ug). The requisite positive charges required to neutralize the DNA was supplied by spermidine. The complex was prepared with or without 170 nmoles of DOPE. The complex was added to CV-1 cells and the luciferase activity measured as described in Example 1. The results are given in Table 1 below, with luciferase activity expressed as light units/mg cell protein. The first activity was always greater when DOPE was present in the complex. In the absence of DOPE, the sequential replacement of positive charge due to gramicidin S by spermidine leads to a biphasic response. The expression of luciferase initially increased to a value about 100 fold less than the maximal response obtained in the presence of DOPE. When the percent of charge neutralization due to gramicidin S dropped below 25% transfection activity was totally lost. Thus, membrane permeabilization function of gramicidin S is more important than the charge neutralization function.

TABLE 1

Spermidine Charge Neutralization

| % charges brought by GS | w/o lipids | with lipids |
| --- | --- | --- |
| 100 | $4.5 \pm 2 \; 10^3$ | $8.5 \pm 0.7 \; 10^8$ |
| 75 | $4 \pm 2.5 \; 10^5$ | $5 \pm 2 \; 10^8$ |
| 25 | $2 \pm 2.5 \; 10^6$ | $2 \pm 0.5 \; 10^7$ |
| 12.5 | 0 | $2 \pm 0.5 \; 10^7$ |

F. Use of Other Positively Charged Peptides

The peptide-DOPE-DNA complex was prepared as described in Example 1 except the type of peptide added to the complex was varied at constant amounts of DNA (20 ug) and DOPE (170 nmoles). The peptides employed were polymyxin B, a cyclic cationic peptide; polylysine, a linear cationic peptide; tyrocidine, a cyclic cationic peptide with a similar structure to gramicidin S but containing only a single positive charge and gramicidin S. The luciferase plasmid was also transfected into the cells using Lipofectin™. The complex was added to CV-1 cells and the luciferase activity measured as described in Example 1. FIG. 7 shows that gramicidin S induced the greatest level of expression followed closely by the related cyclic peptide tyrocidine. Both cyclic peptides were superior to Lipofectin™ at transferring the DNA into cells. Activity was also seen with the other two peptides, polymyxin B and polylysine, however, the level of luciferase expression mediated by these two cationic peptides was inferior to that induced by gramicidin S or tyrocidine.

G. Comparison of DNA-Dendrimer Complex and DNA-Polylysine Complex-Mediated Transfections To find better chemically-defined alternatives to the polyamine polymers such as polylysine, we have employed the hydrophilic branched polycation macromolecules also know as the Starburst™ Dendrimer microparticles, Tomalia et al., supra, to form a complex with DNA or with DNA and the permeabilizing amphipathic peptide GALA SEQ ID NO:10. R. Parente et al., Biochemistry (1990) 29:8720–8728. The complex was prepared by diluting 12 μg of pCLuc4 plasmid in 660 μl of HBS (20 mM Hepes, 150 mM NaCl, pH 7.4) in a polystyrene tube. Polylysine (Sigma Chemical Co.) or Starburst™ Dendrimer microparticles of the fifth generation (1 nmole) (Polysciences, Inc.) was dissolved in 340 μl of HBS and added slowly (dropwise) to the DNA solution. In these conditions, the positive charges from the epsilon amino groups of the polylysines or from the peripheral amines of the dendrimers are in 1.3-fold excess over the negative charges of the plasmids. When the peptide GALA SEQ ID NO:10 was added, it was added so that the negative charges on GALA SEQ ID NO:10 neutralized the excess charges on the dendrimer. The mixture was left to stand for thirty minutes after the last addition at room temperature and then 500 μl of the mixture was added to CV-1 cells. The transfection protocol was carried out as described above. In this experiment, the best transfection protocol was accomplished with the GALA SEQ ID NO:10-dendrimer-DNA complex, followed by the dendrimer-DNA and then by polylysine-DNA. The results are shown in Table 2 below.

TABLE 2

DNA-Dendrimer Mediated Transfection

| Condition | Luciferase lights (units per mg cell protein) |
|---|---|
| Dendrimer-GALA SEQ ID NO:11-DNA | $(9 \pm 2) \times 10^5$ ($\underline{n}$ = 2) |
| Dendrimer-DNA | $(5 \pm 2) \times 10^5$ ($\underline{n}$ = 2) |
| Polylysine-DNA | $(2.7 \pm 0.1) \times 10^5$ ($\underline{n}$ = 2) |

EXAMPLE 2

Synthesis of Reactive and Functionalized Spermidine Bis-Acridines

Spermidine bis-acridine derivatives (synthesis shown in FIG. 8) intercalate into double stranded nucleic acids with affinity constants greater than $1 \times 10^4$ (pH 7.4; 0.2M NaCl) and can be used to attach a variety of targeting molecules to DNA. Carbohydrates, peptides, hormones, vitamins, cofactors, proteins or antibodies can all be used as targeting ligands.

A. Spermidine Bis-Acridine

The scheme for directing nucleic acids to certain sites of the body is based upon the intercalation of a ligand which interacts with a cell surface component into the double stranded DNA. A procedure for selective $N^4$-acylation of spermidine, using $N^1,N^8$-bis(t-butoxycarbonyl) spermidine as starting material, has been reported. R. J. Bergeron et al., Synthesis (1982) 689–692. We have used this procedure (FIG. 8) to link the acid functionalized galactosyl derivatives 9(n=1) and 9'(n=4) to the secondary amino group of $N^1,N^8$-tBoc-protected spermidine (15) and the resulting galactosylated spermidines 17 and 17' were, after deprotection, further alkylated with 9-phenoxyacridine by a standard chemical procedure to transform them into bis-intercalator compounds 21 and 21'. The synthesis of the carboxylic acid functionalized galactosyl derivatives is detailed (J. Haensler et al., Biochim Biophys Acta (1988) 946:95–105) and is easily applicable to a wide range of carbohydrate ligands (M. M. Ponpipom et al., J Med Chem (1981) 24:1388–1395). The title compounds were obtained in an overall yield of 30% and the NMR and mass spectrometry data are consistent with the proposed structure.

B. Activated Spermidine Bis-Acridine

Based upon the above scheme, a versatile method for attaching peptides to a spermidine bis-acridine derivative, has been developed. $N^1,N^8$-bis(t-butoxycarbonyl) spermidine (15) was $N^4$-acylated with N-succinimidyl-4-(p-maleimidophenyl)butyrate (SMPB) (4), deprotected and coupled to acridine to make a bis-intercalator bearing a maleimide group (20). A single compound was obtained after chromatographic purification on silica gel in 25% overall yield. The NMR and mass spectrometry results are consistent with the assigned structure.

C. Spermidine Bis-Acridine Linked to a NLS

The NLS peptide SEQ ID NO:1 (Kaneda et al., supra, Science (1989) 243:375–378) and control peptides with the same composition but a different sequence have been synthesized on an ABI automatic peptide synthesizer with an N-terminal cysteine residue. The cysteine peptide is then attached to the maleimide bearing intercalator (FIG. 9) and can be anchored into double stranded nucleic acids.

D. Biodegradable Linkers

Biodegradable linkers consisting of a lys-lys peptide linkage are synthesized in the manner. shown in FIG. 10. In the figure, a galactose residue is placed on the unprotected amine. Alternatively, a protected peptide containing two adjacent lysine residues is synthesized by solid phase synthesis. The peptide carries membrane permeabilization functions or targeting functions and acridine residues are added to the two ε-amino groups on the lysines.

EXAMPLE 3

Gel Retardation Assay of pCLuc4 Plasmid with Galactosylated Intercalators and Agglutinin To demonstrate that the galactosylated bis-acridines 21 and 21' of Example 2 (21' is the homolog of 21 where the galactose is separated from spermidine bis-acridine by three extra carbons) can interact with a soluble receptor while attached to DNA, we used a gel shift assay. In this assay, a galactose binding protein, Ricinus Communis lectin $RCA_{120}$, was incubated with the galactosyl-bis-acridine-DNA complex. If this protein interacts with the complex and the complex remains associated with the DNA, the DNA does not migrate into the electrophoresis gel. Each sample of the plasmid pCLuc4 (2 μl; 140 ng) was mixed with 13.5 pmoles of 21 or 21' and then 1 μl (33.3 pmoles) of $RCA_{120}$ was added, plus when indicated, an excess of free galactose (1.35 nmoles). After 30 minutes of incubation at room temperature, the samples were electrophoresed through a 0.8% agarose gel using a 0.04 M Tris-Acetate buffer system (pH 7.6) and stained with ethidium bromide to visualize the DNA (FIG. 11).

Intercalation of the galactosylated spermidine bis-acridines into the pCLuc4 plasmid is shown by the retardation observed for the plasmid when complexed with compounds 21' (lane B) or 21 (lane E). Intercalation of the bis-acridine into the DNA produces a change from the supercoiled form to a relaxed circular form, which migrates slower.

The capability of the plasmid-galactose complex to bind to a soluble receptor for galactose is shown by the almost complete retardation of the complex in presence of *Ricinus Communis* lectin $RCA_{120}$ (lane C and F). $RCA_{120}$ is a dimer and has two binding sites selective for terminal β-D-galactosyl residues and thus too can crosslink the plasmid-galactose complexes. The interaction of $RCA_{120}$ with the plasmid pCLuc4 when complexed to compounds 21 or 21' results in a formation of large aggregates which do not penetrate into the gel. This interaction appears to be much more efficient when the plasmid is complexed with 21' than with 21. To crosslink the plasmids, $RCA_{120}$ has to overcome electrostatic repulsions existing between adjacent plasmids. Thus, separating the galactose from the surface of the plasmids by a spacer arm, as in case of the complexes obtained with compound 21', makes the binding of the lectin easier. As a result of a multivalent interaction, the plasmid aggregates formed by $RCA_{120}$ are very stable and are not dissociated by a 100-fold excess of a competing monovalent ligand such as galactose (lanes D and G).

EXAMPLE 4

Binding of Bis-acridines to Double-Stranded DNA Using Ethidium Bromide Displacement Assay The affinity of the bis-acridines for calf thymus DNA was calculated from the displacement of ethidium bromide from double stranded nucleic acids (Nielsen, supra). Ethidium displacement was monitored by the decrease of the ethidium bromide fluorescence (ex.=540 nm, em.=610 nm) that occurs when it is released from DNA. The association constants of the bis-acridines relative to ethidium bromide are calculated from their $IC_{50}$. In this study, spermidine bis-acridine trihydrochloride (SBA•3HCl) synthesized as described (Nielsen, supra), was used as the reference compound. As a result of the loss of one of its three positive charges, a slight but significant decrease in affinity is observed when the $N^4$ amino group of spermidine bis-acridine is engaged in an amide bond with the targeting carbohydrate in compound 21 (Gal-bA•2 HCl). However, we predict an increase in affinity when spermidine bis-acridine is linked to the highly positively charged NLS peptide SEQ ID NO:1. G. Karup et al., *Int J Peptide Protein Res* (1988) 32:331–343.

The binding constants of the various bis-acridine conjugates synthesized to attach targeting ligands to DNA in the various examples are given in Table 3.

TABLE 3

Dissociation Constants of the Bis-acridines from Calf Thymus DNA (in M)

| | |
|---|---|
| SBA · 3HCl | $2.4 \times 10^{-8}$ |
| Gal-3-bA[1] | $3.5 \times 10^{-7}$ |
| Gal-6-bA[2] | $7.9 \times 10^{-7}$ |
| Gal$_3$Lys$_2$-bA[3] | $5.4 \times 10^{-6}$ |
| Maleimido-bA[4] | $6.5 \times 10^{-7}$ |
| WTcys-bA[5] | $1.4 \times 10^{-7}$ |
| SNL-bA[6] | $1.4 \times 10^{-7}$ |

[1]Compound 21 where n = 3
[2]Compound 21 where n = 6
[3]Compound 26 (shown in Example 6)
[4]Compound 20
[5]SBA linked to SEQ ID NO:8
[6]SBA linked to SEQ ID NO:9

The binding constants for the various bis-acridines are computed from an ethidium bromide displacement assay by using a method to determine the binding affinity of a 4-Mer for a linear lattice via noncooperative competitive binding with a 2-Mer (A. Wolfe and T. Meehan. *J.Mol.Biol.* 223, 1063–1087, 1992) and an intrinsic dissociation constant of $5.3 \times 10^{-6}$M for ethidium bromide.

EXAMPLE 5

Ability of Bis-acridine Galactosyl Ligands to Target DNA to Cell-surface Receptors To demonstrate the factors that control targeting ability of the bis-acridine intercalators containing a galactosyl targeting ligand, rat hepatocytes were isolated from rat liver and placed in culture at a density of $10^6$ hepatocytes in 60 mm petri dishes in 3 ml of minimum essential medium (MEM) medium containing 5% fetal calf serum and antibiotics. The hepatocytes are shown to have galactose receptors by binding asialoorosomucoid. After 18 hours at 37° C., the medium is removed and replaced with 1 ml of MEM. Then 1 ug of $^{125}$I-labeled plasmid DNA complexed to either SBA•3HCL, Gal-3-bA, Gal-6-bA or Gal$_3$-Lys$_2$-bA in 100 ul water was added to the culture dish. The intercalator to plasmid ratio was 500:1 or 1000:1. The cells were incubated for an additional hour at 37° C., then rinsed and the protein digested in 1 ml NaOH (1N). The cell lysate was counted for radioactivity and the protein measured. The amount of cell associated plasmid is expressed as ng of plasmid per mg of cell protein and graphed as a function of complexing agent (FIG. 12). Although all three galactosyl bis acridine compounds bind to DNA (Table 3) and can interact with a soluble galactose binding protein (Example 3), only the Gal$_3$-Lys$_2$-bA was able to interact with the cell surface receptor. Thus, efficient targeting to cell surface receptors requires a longer spacer arm and/or a cluster of galactosyl residues as provided by the Gal$_3$-Lys$_2$-bA (synthesis shown in FIG. 13 and Example 6).

EXAMPLE 6

Synthesis of a Biodegradable Bis-acridine Containing Three Targeting Ligands: Trigalactosylated Spermidine Bis-acridine The complete synthesis of this molecule is shown in FIG. 13.

Synthesis of L-Lysyl-L-Lysine bis-trifluoroacetate(22): Nε-tBOC-L-Lysine (603 mg, 2.45 mmol) and Nα,Nε-bis-tBOC-L-Lysine-p-nitrophenyl ester (2.28 g; 4.9 mmol) were mixed in 40 ml of N-methyl morpholine containing 640 μl of N,N diisopropylethylamine (3.7 mmol). The mixture was stirred overnight at room temperature under argon filtered to remove insoluble traces of unreacted Nε-tBOC-L-Lysine and evaporated to dryness under high vacuum. The residue was purified in a silica gel column eluted with the system $CHCl_3/CH_3OH/H_2O$ 9:1:0.1, to afford 1.22 g of pure tBOC-protected Lysine dimer; yield 87%

Deprotection: To a cooled flask (dry ice) containing 700 mg (1.2 mmol) of the tBOC-protected Lysine dimer were added 5 ml of TFA. The mixture was warmed to room temperature and stirred under argon. After 30 minutes stirring the trifluoroacetic acid was evaporated in vacuo. The residue was taken up in acetone and evaporated (5 times). Finally the residue was redissolved in 14 ml of water, washed three times with 8 ml of chloroform and the residue was lyophilized to give 480 mg of the title compound; yield 80%.

Protected trigalactosyl lysine dimer: Synthesis, of Nα-[Nα, Nε-Bis[6-(1-thio-2,3,4,6,-tetra-O-acetyl-β-D-galactopyranosyl)hexanoyl]-L-Lysyl-Nε-[6-(1-thio-2,3,4,6,-tetra-O-acetyl-β-D-galactopyranosyl)hexanoyl]-L-Lysine (23).

To a solution of L-Lysyl-L-Lysine bis-trifluoroacetate (400 mg; 0.8 mmol) in 8 ml of anhydrous DMF containing 505 μl of triethylamine (3.6 mmol) was added p-nitrophenyl 6-(1-thio-2,3,4,6,-tetra-O-acetyl-β-D-galactopyranosyl) hexanoate (1.44 g; 2.4 mmol). The mixture was stirred overnight under argon and evaporated to dryness. The residue was purified by chromatography on a silica gel column eluted with $CHCl_3/CH_3OH/H_2O$ 90:10:0.5, to give 463 mg of the title compound; yield 35%.

MS: Calculated for $C_{72}H_{109}N_4O_{32}S_3$ m/z=1653, found m/z=1653.6 (M+H)+, m/z=1677.6 (M+Na)+, m/z=1693.6 (M+K)+.

Reaction with selectively blocked spermidine: N4-(Nα-[Nα,Nε-Bis[6-(1-thio-2,3,4,6,-tetra-O-acetyl-β-D-galactopyranosyl)hexanoyl]]-L-Lysyl-Nε-[6-(1-thio-2,3,4,6,-tetra-O-acetyl-β-D-galactopyranosyl)hexanoyl]-L-Lysyl]-N1,N8-bis-tBOC-spermidine.(24).

Compound 23 (132 mg; 80 μmol) was activated by esterification with N-Hydroxysuccinimide (11 mg, 96 μmol) in the presence of N,N'-dicyclohexylcarbodiimidide (DCC) (20 mg; 97 μmol) in 5 ml of anhydrous methylene chloride. After 4 h stirring at room temperature under argon, the urea precipitate was removed by filtration and the filtrate was evaporated in vacuo. The dry residue was redissolved in 3 ml of acetonitrile and added dropwise to a solution of N1,N8-bis(t-butoxycarbonyl spermidine) Hydrochloride (30 mg; 80 μmol) in 3 ml of acetonitrile containing 14 μl of triethylamine (100 μmoles). The mixture was further stirred for 48 h at room temperature under argon, evaporated in vacuo to a residue which was purified on a silica gel column, eluted with $CHCl_3/CH_3OH/H_2O$ 90:10:1, to afford 71 mg of the title compound; yield 45%.

Deprotection: Synthesis of N4-[Nα-[Nα,Nε-bis[6-(1-thio-β-D-galactopyranosyl)hexanoyl]]-L-Lysyl-Nε-[6-(1-thio-β-D-galactopyranosyl)hexanoyl]]-L-Lysyl] spermidine.(25) Compound 24 (71 mg; 36 μmol) was deprotected as described previously for compound 17 (See Example 2.A). The tBOC protecting groups were removed from the spermidine linker by treating with 5 ml of TFA for 30 min and the acetyl protecting groups were removed from the galactosyl headgroups by treating overnight with a mixture of $CH_3OH/NEt_3/H_2O$ 5:4:1. The bis-trifluoroacetate salt of the spermidine derivative was converted to the free amine by passing a water solution of the salt through a small BIO-RAD AG 1×2 (OH⁻) column. The fractions positive for carbohydrates and for amines were pooled together and lyophilized to give 36 mg of compound 25); yield 79%.

Acridine attachment: Synthesis of N4-[Nα-[Nα,Nε-bis[6-(1-thio-β-D-galactopyranosyl)hexanoyl]]-L-Lysyl-Nε-[6-(1-thio-β-D-galactopyranosyl)hexanoyl]]-L-Lysyl)-N1,N8-bis-acridine spermidine.(26) ("Gal₃-Lys₂-bA") Compound 25 (36 mg; 28.5 μmol) and 18 mg of 9-phenoxyacridine were dissolved in 3 g of phenol at 80° C. and the solution was further stirred for 2 h at 80° C. under argon. The mixture was then cooled to about 40° C. and poured into 15 ml of ether to precipitate the aminoacridines. The yellow precipitate was collected by filtration on a filter paper and redissolved in 4 ml of a butanol/methanol mixture 3:1. This solution was then concentrated by evaporation to about 1 ml and the bis-acridine derivative was isolated by chromatography on a silica gel column, eluted with n-Butanol/Pyridine/Acetic acid/Water 6:2:1:2.

34 mg of the title compound are obtained; yield 21%. MS: Calculated for $C_{81}H_{117}N_9O_{20}S_3$ m/z=1631, found m/z=1632.8 (M+H)+, m/z=1654.8 (M+Na)+.

EXAMPLE 7

Transfection Assay Using Nuclear Localization Sequences

5 μl of Tris-EDTA(TE) containing a trace amount of a 5 Kb radioiodinated plasmid (CMV-βGal) and 50 μl of water containing 8 nmoles of the nuclear localization peptide-bis-acridine conjugate of Example 2-C were added to 80 μg of pCLuc4 (123 neq. bp) in solution in 45 μl of TE buffer (pH 8). The ratio of plasmid to peptide conjugate was 1:300. After 1 hour standing at room temperature 100 μl of Tris-Cl buffer (pH 9) was added to the complex and the resulting solution was mixed with 12 pmoles of lipids (DOPE/CHEMS 2:1, molar ratio) dissolved in 600 μl of ether for the preparation of pH-sensitive liposomes.

The vesicles containing the DNA-peptide complexes were separated from nonencapsulated material by floating the liposomes through a Ficoll gradient. Encapsulation efficiency (20%±4%) was determined by dynamic light scattering (Coulter N4, Coultronics).

Cells were transfected with 4 μg of liposome-encapsulated plasmid (100 μl of the liposome solution) for 5 hours at 37° C. and luciferase activity was counted after 48 hours in a bioluminometer. Table 4 shows the measured light units/mg cell protein as a function of the liposomal content. The values are the averages of three determinations.

TABLE 4

| | Liposomal Content | |
|---|---|---|
| Plasmid Alone | Plasmid-WTcys-bA Complex | Plasmid-SNL-bA Complex |
| $(0.32 \pm 0.02) \, 10^6$ | $(0.82 \pm 0.36) \, 10^6$ | $(1.36 \pm 0.28) \, 10^6$ |

Positive control: Lipofectin ® = $(1.4 \pm 0.2) \, 10^8$.

Assuming that the pH-sensitive liposomes deliver their content into the cytoplasm of the host cell, the naked plasmid must be able to penetrate the nucleus.

Assuming, hypothetically that the peptide-bis-acridines conjugates do not protect DNA from degradation, the observed transfection enhancement must be the result of increased nuclear entry. The 4-5 fold increase of transfection agrees with published results (Kaneda et al., supra *Science* (1989) 243:375–378) using proteins that bind to DNA and enhance DNA entry into the nucleus. Both the SNL peptide and WTcys peptide increase expression and are a convenient technique to target DNA into the nucleus.

EXAMPLE 8

Synthesis of Cationic Bile Salts

A. Preparation of the α-cholic Acid Amide of Nα-benyzlester Nε-tBOC-Lysine

The synthesis is based upon that of S. Bergstrom et al., *Acta Chem Scand* (1953) 7:1126. 204 mg (0.500 millimoles) of cholic acid was weighed into a screw-capped test-tube, and 2.5 ml dioxane and 70 microliters (0.500 millimoles) of triethylamine was added to the tube. The mixture was cooled in an ice bath until the solution solidified (at about 12° C). 65 microliters (0.500 millimoles) of isobutyl chloroformate were added, the reaction tube was agitated and returned to the ice bath. The tube was alternatively removed and replaced in the bath to keep the temperature at the point of incipient solidification for 30 minutes.

Nα-benyzlester, Nε-tBOC-Lysine (0.500 millimoles) and 70 microliters (0.500 millimoles) of triethylamine were suspended in 0.6 ml of water. The mixture was cooled in the ice bath, added to the dioxane reaction mixture, and the container rinsed into the reaction mixture with another 0.5 ml of ice water. The tube stood in the ice bath for ½ hour and then was permitted to warm to room temperature.

Most of the organic solvent was evaporated beneath a stream of argon gas, and the residue was brought up to 3 ml with water. 5% aqueous sodium carbonate was added in a dropwise fashion until the pH reached 9. The mixture was extracted with three successive 3 ml portions of ethyl ether, and the aqueous phase saved.

To the aqueous residue, 0.5 N hydrochloric acid was added until the pH fell to 4. The mixture was extracted with three successive 3 ml portions of ethyl ether, and the aqueous phase saved.

The pH of the aqueous residue was readjusted to 4 with 0.5 N hydrochloric acid and extracted into five successive 3 ml portions of ethylacetate. These ethylacetate extracts were combined and evaporated to dryness under vacuum to obtain 284 mg of colorless powder melting. The tBOC protecting group for the ϵ-amine was removed by standard methods to yield the positively charged lysine derivative of cholic acid. In a similar fashion other positively charged derivatives of cholic acid can be prepared.

B. Preparation of Cholic Acid Amide of Tris (2-aminoethyl) amine

When multiple amine groups are available for coupling to the activated cholic acid the amine is added in a 6 fold excess over the activated bile salt prepared as described in Example 8-A. The synthesis is based upon that of Bergstrom et al., supra. Weigh 204 mg (0.500 millimoles) of cholic acid into a screw-capped test tube. Add 2.5 ml dioxane and 70 microliters (0.500 millimoles) of triethyl amine. Cool in an ice bath until the solution commences to solidify (at about 12° C.). Add 65 microliters (0.500 millimoles) of isobutyl chloroformate and after agitating, return the reaction tube to the ice bath. By alternately removing from the ice bath and replacing in the bath, keep the temperature at the point of incipient solidification for 30 minutes.

Add (3.00 millimoles) of tris(2-aminoethyl)amine and 70 microliters (0.500 millimoles) of triethylamine in 0.6 ml of water. Cool in the ice bath, add to the dioxane reaction mixture, and rinse the container into the reaction mixture with another 0.5 ml of ice water. Let stand in the ice bath for ½ hour and then permit to warm to room temperature.

Evaporate most of the organic solvent beneath a stream of argon gas. Make the residue back up to 3 ml with water. Add 5% aqueous sodium carbonate dropwise until the pH reaches 7. Extract with three successive 3 ml portions of ethyl ether, saving the aqueous phase.

To the aqueous residue add 0.5 N hydrochloric acid until the pH falls to 4. Extract with three successive 3 ml portions of ethyl ether, saving the aqueous phase.

Readjust the pH of the aqueous residue to 4 with 0.5 N hydrochloric acid and extract into five successive 3 ml portions of ethylacetate. Combine these ethyl acetate extracts and evaporate to dryness under vacuum to obtain the cholic acid amide of tris(aminoethyl)amine.

EXAMPLE 9

Synthesis of Polyethyleneglycol-bis-Acridine

The synthesis of PEG-coupled bis-acridine spermidine follows standard chemistry and involves the following steps:

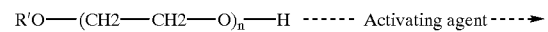
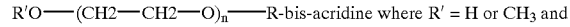

R* = activating group and n = 10–250, preferably 20–60.

There are many methods for preparing activated monomethoxy PEG molecules or activated PEG molecules. A preferred method has been described by D. Larwood and F. Szoka, *J Labelled Comp & Radiopharm* (1984) 21:603–614. Polyethylene glycol 1900 carbonyl-imidazole methyl ether was prepared by taking 530 mg (0.28 mmol) dry PEG 1900 monomethyl ether in 2 ml dry methylene chloride and adding 78 mg (0.46 mmol) carbonyldiimidazole and 10 mg (0.11 mmole) imidazole (sodium salt). After stirring overnight, 6 ml dry methylene chloride were added and the mixture extracted with 3.75 ml water, then dried with anhydrous sodium sulfate. After filtration, the solvent was removed, with quantitative yield. Alternatively, the solvent was removed, and the resulting oil recrystallized from chloroform/diethyl ether at −20° C. The resulting imidazole carbamate white crystals were filtered through a chilled funnel, rinsed with a small amount of diethyl ether, and used immediately.

The imidazole carbamate (0.1 mM) is added to 0.125 mM of N,N'-bis-(9-acridinyl)-4-aza-1,8-diaminooctane ("bis-acridine spermadine", prepared as described by P. Nielsen, Eur. J. Biochem. 122:283–289, 1992), dissolved in phenol and the reaction run at 80° C. under argon for 2 hours. The mixture is taken to dryness and the yellow product washed with cold ethanol and then diethyl ether. The PEG is coupled via a carbamate linkage to the secondary amine of the bis-acridine spermidine to form the monomethoxy PEG-bis-acridine spermidine and is soluble in water.

In a similar fashion the non-blocked PEG (molecular weight 6000), is activated as above to form the bis-imidazole carbamate PEG. The bis-imidazole carbamate PEG is reacted with a 2.5 fold excess of bis-acridine spermidine to form the bis(bis-acridine spermidine)-PEG 6000.

Various types of activators for PEG and monomethoxy PEG have been described in U.S. Pat. No. 5,013,556 to Woodle et al. These methods can be used to generate reactive PEGs that can be attached to the bis-acridine molecule via a variety of chemistries. For instance a sulf-hydryl containing monomethoxy-PEG can be attached to the maleimide-containing bis-acridine of Example 2-B.

EXAMPLE 10

DNA-Masking with PEG-bis-acridine

PEG molecules can be used to mask the surface of the DNA and permit the DNA to circulate for a longer period. Radio-iodinated plasmid DNA is mixed with monomethoxy-PEG-1900-bis-acridine spermidine as synthesized in Example 9 at a 20 bp DNA-to-I PEG molecule ratio, for 30 minutes at room temperature. An aliquot of the complex, 5 μg DNA in 0.2 ml PBS, is injected via the tail vein into each of a group of 12 mice. Mice are sacrificed at various periods after injection. The blood and other organs are removed and the radioactivity associated with each organ is determined. DNA which has not been complexed to the monomethoxy-PEG-bis-acridine-spermidine is injected into a second group of mice (control mice). After 10 minutes, 15% of the radioactive plasmid DNA remains in the blood in the control mice, whereas in the monomethoxy PEG-bis-acridine spermidine DNA group significantly greater levels of the radio-labeled plasmid-PEG complex remain in circulation. This indicates a pronounced masking effect of the DNA molecule by the PEG-bis-acridine spermidine.

EXAMPLE 11

Synthesis of a Lecithin Acyl Amine Masking Reagent

The synthesis of polynucleotide masking lipids is accomplished by standard chemistry such as that described in C. Pidgeon et al., *Anal Biochem* (1989) 176:36–47.

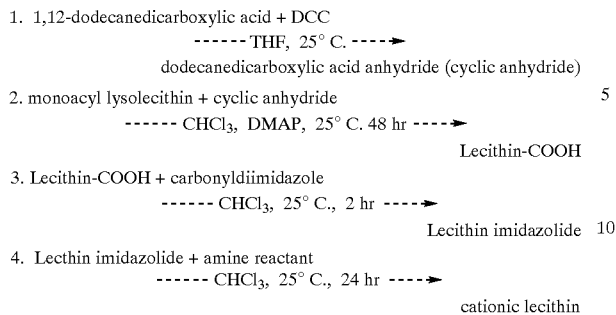

The final reaction of the amine reactant with the lecithin imidazolide is undertaken immediately after formation of the lecithin imidazolide. The lecithin imidazolide (0.1 mM) is added to a solution of the amine (0.7 mM) in chloroform. Suitable amines for this coupling are listed in this specification.

After two hours at room temperature the reaction mixture is added to a two-fold volume of water/methanol and the pH is adjusted to 10. The lecithin linked amine is extracted into the organic phase. The organic phase is then washed with 0.1 M sodium chloride and the organic phase taken to dryness. The resulting acyl amine lecithin is used to mask the surface of the polynucleotide. Various lysolecithin molecules can be used to prepare the lecithin-COOH, including lauroyl, myristoyl, palmitoyl, oleoyl or phytanoyl, or stearoyl. Other headgroups such as ethanolamine or phosphatidic acid can be substituted for lecithin if they are suitably protected in the activation steps and deprotected at the end of the reaction.

EXAMPLE 12

DNA-Masking with Lecithin Acyl Amine

The lecithin acyl amine of Example 11 can be added to DNA from an ethanol solution at a ratio of 1 positive charge to each phosphate group on the DNA. The molecule can be used to mask the surface of the DNA and permit the DNA to circulate for a longer period. An aliquot of the complex, 5 $\mu$g DNA in 0.2 ml PBS, is injected via the tail vein into each of a group of 12 mice. Mice are sacrificed at various periods after injection. The blood and other organs are removed and the radioactivity associated with each organ is determined. DNA which has not been complexed to the lecithin acyl amine is injected into a second group of mice (control mice). After 10 minutes, 15% of the radioactive plasmid DNA remains in the blood in the control mice, whereas in the lecithin acylamine group significantly greater levels of the radiolabeled plasmid-lecithin complex remain in. This indicates a pronounced masking effect of the DNA molecule by the lecithin acyl amine.

We claim:

1. A composition for presenting a polynucleotide to a subcellular component of a eukaryotic cell comprising:
    a) a polynucleotide; and
    b) three or more functional agents associated with the polynucleotide, the agents being selected from the group consisting of:
        i) a cell recognition agent capable of recognizing the eukaryotic cell, said agent comprising a ligand for a receptor located on the eukaryotic cell surface and a DNA-associating moiety being coupled thereto, the DNA-associating moiety being selected from the group consisting of a single stranded polynucleotide linker, a dendrimer polycation, a major-or minor groove binder, and an intercalating agent;
        ii) a membrane-permeabilizing agent capable of transporting the polynucleotide across the cytoplasmic membrane of the eukaryotic cell;
        iii) a subcellular-localization agent capable of delivering the polynucleotide from the cytoplasm of the eukaryotic cell to a subcellular component of the eukaryotic cell, said agent further comprising a DNA-associating moiety being coupled thereto, the DNA-associating moiety being selected from the group consisting of a single stranded polynucleotide linker, a dendrimer polycation, a major-or minor groove binder, and an intercalating agent; and
        iv) a polynucleotide-masking agent capable of increasing the circulatory half-life of the desired polynucleotide.

2. A composition for presenting a polynucleotide to a subcellular component of a eukaryotic cell comprising:
    a) a polynucleotide;
    b) an agent operatively coupled to the polynucleotide, the agent being selected from the group consisting of
        i) a cell recognition agent capable of recognizing the eukaryotic cell, said agent comprising a ligand for a receptor located on the eukaryotic cell surface and a DNA-associating moiety being coupled thereto, the DNA-associating moiety being selected from the group consisting of a single stranded polynucleotide linker, a dendrimer polycation, a major-or minor-groove binder, and an intercalating agent;
        ii) a membrane-permeabilizing agent capable of transporting the polynucleotide across the cytoplasmic membrane of the eukaryotic cell; and
        iii) a subcellular-localization agent capable of delivering the polynucleotide from the cytoplasm of the eukaryotic cell to a subcellular component of the eukaryotic cell; and
    c) a DNA masking agent capable of increasing the circulatory half-life of the polynucleotide, wherein the DNA-masking agent has the chemical formula $$\begin{array}{c}R^3\\ \diagdown\\ N-\underset{\underset{O}{\|}}{C}-(CH_2)_n-\underset{\underset{O}{\|}}{C}-O-\underset{|}{CH}-CH_2-O-\underset{\underset{O}{|}}{\overset{\overset{O}{\|}}{P}}-Y\\ \diagup\\ R^4\end{array}\qquad \begin{array}{c}\overset{\overset{O}{\|}}{R^1-C-O-CH_2}\\ |\\ \end{array}$$

wherein n is an integer of 6 to 24;

Y is selected from the group consisting of hydroxy, ethanolamine, choline, glycerol, serine and inositol;

$R^1$ is ($C_6$–$C_{24}$) is alkyl or ($C_6$–$C_{24}$) alkenyl;

$R^3$ is H, or ($C_1$–$C_{10}$) alkyl or ($C_1$–$C_{10}$) alkylamine; and $R^4$ is a positively charged linear or branched ($C_1$–$C_{30}$) alkyl or ($C_1$–$C_{30}$) alkylamine, wherein one or more of the carbon atoms may be substituted with NR', wherein R' is H or ($C_1$–$C_{10}$) alkyl or ($C_1$–$C_{10}$) alkylamine.

3. A composition for presenting a polynucleotide to a subcellular component of a eukaryotic cell comprising
   a) a polynucleotide;
   b) an agent operatively coupled to the polynucleotide, the agent being selected from the group consisting of
      i) a cell recognition agent capable of recognizing the eukaryotic cell, said agent comprising a ligand for a receptor located on the eukaryotic cell surface and a DNA-associating moiety being coupled thereto, the DNA-associating moiety being selected from the group consisting of a single stranded polynucleotide linker, a dendrimer polycation, a major-or minor groove binder, and an intercalating agent;
      ii) a membrane-permeabilizing agent capable of transporting the polynucleotide across the cytoplasmic membrane of the eukaryotic cell; and
      iii) a subcellular-localization agent capable of delivering the polynucleotide from the cytoplasm of the eukaryotic cell to a subcellular component of the eukaryotic cell; and
   c) a DNA masking agent capable of increasing the circulatory half-life of the polynucleotide, wherein the masking agent comprises polyethylene glycol (PEG) covalently linked to a DNA-associating moiety.

4. A composition for presenting a polynucleotide to a subcellular component of a eukaryotic cell comprising
   a polynucleotide;
   a membrane-permeabilizing agent capable of transporting the polynucleotide across the cytoplasmic membrane of the eukaryotic cell operatively coupled to the polynucleotide, wherein the membrane-permeabilizing agent comprises an amphipathic peptide; and
   a lipid or a polyamine.

5. The composition of claim 4, wherein the amphipathic peptide comprises GALA/SEQ ID NO: 10.

6. The composition of claim 4, wherein the peptide comprises a cyclic peptide.

7. The composition of claim 6, wherein the cyclic peptide is selected from the group consisting of gramicidin S and tyrocidines.

8. The composition of claim 7, wherein the cyclic peptide comprises gramicidin S.

9. A composition for presenting a polynucleotide to a subcellular component of a eukaryotic cell comprising
   a polynucleotide; and
   a cell recognition agent operatively coupled to the polynucleotide and capable of recognizing the eukaryotic cell, said agent comprising a ligand for a receptor located on the eukaryotic cell surface and a DNA-associating moiety being coupled thereto, the DNA-associating moiety comprising an intercalating agent, wherein the intercalating agent has the formula

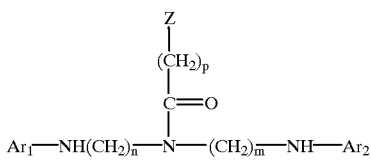

wherein
   Z comprises a bond, a reactive group selected from the group consisting of N-hydroxysuccinimide, maleimide, maleimidophenyl, pyridyl disulfide, hydrazide, and phenylglyoxal, or ZY, wherein Y is selected from the group consisting of cell surface receptor ligands, nuclear localization sequences, and membrane permeabilizing components;
   n and m are independently an integer of 1 to 20;
   p is an integer of 0 to 20; and
   $Ar_1$ and $Ar_2$ are independently selected from the group consisting of ethidium bromide, acridine, mitoxanotrone, oxazolopyridocarbazole, ellipticine, N-methyl-2, 7-diazapyrenium, and derivatives capable of intercalating a polynucleotide.

10. The composition of claim 9, wherein the intercalating agent is coupled to a plurality of ligands.

11. A composition for presenting a polynucleotide to a subcellular component of a eukaryotic cell comprising
    a polynucleotide; and
    a cell recognition agent operatively coupled to the polynucleotide and capable of recognizing the eukaryotic cell, said agent comprising a ligand for a receptor located on the eukaryotic cell surface and a DNA-associating moiety being coupled thereto, the DNA-associating moiety comprising an intercalating agent, wherein the intercalating agent comprises the trigalactosylated spermidine bis-acridine compound (26) of FIG. 13.

12. A composition for presenting a polynucleotide to a subcellular component of a eukaryotic cell comprising
    a polynucleotide;
    a subcellular-localization agent operatively coupled to the polynucleotide and capable of delivering the polynucleotide from the cytoplasm of the eukaryotic cell to a subcellular component of the eukaryotic cell comprising a nuclear localization segment coupled to a DNA-associating moiety, wherein the DNA-associating moiety comprises an intercalating agent having the chemical formula

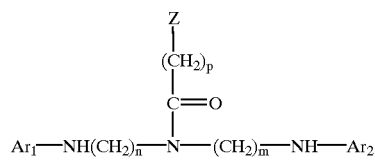

wherein
   comprises a bond, a reactive group selected from the group consisting of N-hydroxysuccinimide, maleimide, maleimidophenyl, pyridyl disulfide, hydrazide, and phenylglyoxal, or ZY, wherein Y is selected from the group consisting of cell surface receptor ligands, nuclear localization sequences, and membrane permeabilizing components;
   n and m are independently an integer of 1 to 20;
   p is an integer of 0 to 20; and
   $Ar_1$ and $Ar_2$ are independently selected from the group consisting of etuidium bromide, acridine, mitoxantrone, oxazolopyridocarbazole, ellipticine, N-methyl-2, 7-diazapyrenium, and derivatives capable of intercalating a polynucleotide.

13. The composition of claim 12, wherein $Ar_1$ and $Ar_2$ comprise acridine.

14. The composition of claim 13, wherein Z comprises the reactive group maleimidophenyl.

15. A composition for presenting a polynucleotide to a subcellular component of a eukaryotic cell comprising a polynucleotide;

a subcellular-localization agent operatively coupled to the polynucleotide and capable of delivering the polynucleotide from the cytoplasm of the eukaryotic cell to a subcellular component of the eukaryotic cell comprising a nuclear localization segment coupled to a DNA-associating moiety, wherein the DNA-associating moiety comprises an intercalating agent having the chemical formula

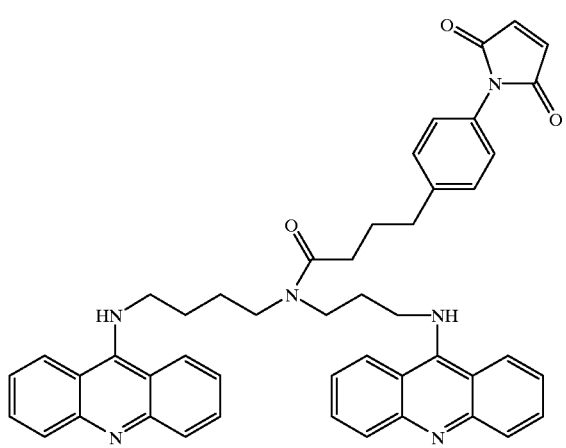

16. The composition of claim 12, wherein Z comprises the group

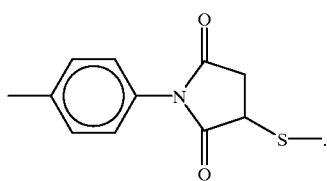

17. A composition for presenting a desired polynucloetide to a subcellular component of a eukaryotic cell comprising:
a) a desired polynucleotide operatively coupled to a polynucleotide-associating moiety selected from the group consisting of:
  i) an intercalator;
  ii) a linker strand comprising a single stranded polynucleotide;
  iii) a dendrimer polycation; and
b) three functional agents operatively coupled to the polynucleotide, the function agents selected from the group consisting of:
  i) a cell recognition agent capable of recognizing the eukaryotic cell;
  ii) membrane-permeabilizing agent capable of transporting the desired polynucleotide across the cytoplasmic membrane of the eukaryotic cell;
  iii) a subcellular-localization agent capable of delivering the desired polynucleotide from the cytoplasm of the eukaryotic cell to a subcellular component of the eukaryotic cell;
  iv) a polynucleotide-masking agent capable of increasing the circulatory half-life of the desired polynucleotide; and
  v) a group to link with one of more of the functional agents i)–iv) by a covalent bond.

18. The composition of claim 17 wherein the polynucleotide-associating moiety comprises an intercalator.

19. The composition of claim 18 wherein the intercalator is coupled to a plurality of the functional agents i)–iv).

20. The composition of claim 18 wherein the intercalator has the formula

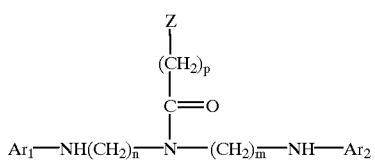

wherein
  Z comprises a reactive group selected from the group consisting of N-hydroxysuccinimide, maleimide, maleimidophenyl, pyridyl disulfide, hydrazide, and phenylglyoxal, or ZY, wherein Y is selected from the group consisting of functional agents i)–iv);
  n and m are independently an integer of 1 to 20;
  p is an integer of 0 to 20; and
  $Ar_1$ and $Ar_2$ are independently selected from the group consisting of ethidium bromide, acridine, mitoxanotrone, oxazolopyridocarbazole, ellipticine, N-methyl-2, 7-diazapyrenium, and derivatives capable of intercalating a polynucleotide.

21. The composition of claim 20 wherein $Ar_1$ and $Ar_2$ each comprise acridine.

22. The composition of claim 21 wherein the intercalator comprises the trigalactosylated spermidine bis-acridine compound (26) of FIG. 13.

23. The composition of claim 20 wherein Z comprises the group maleimidophenyl.

24. The composition of claim 20 wherein Z comprises the group

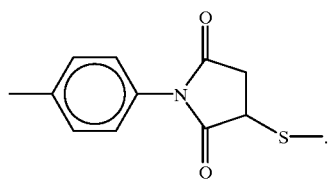

25. The composition of claim 18 wherein the intercalator has the chemical formula

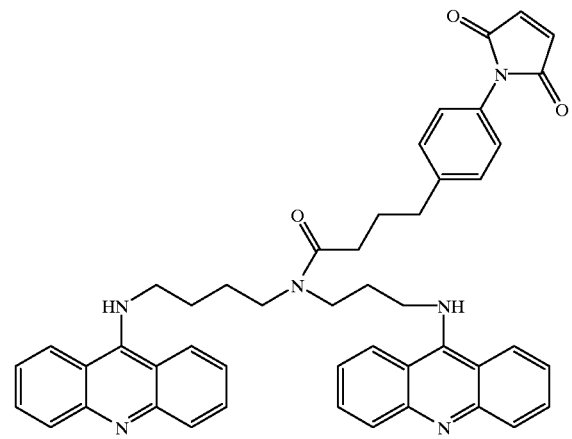

26. The composition of claim 18 wherein the intercalator is biodegradable.

27. The composition of claim 26 wherein the intercalator comprises a peptide sequence and intercalating groups linked to the peptide sequence.

28. The composition of claim 27 wherein the peptide sequence comprises KK.

29. The composition of claim 18 wherein the intercalator has the formula $$(aa)_x\text{—}aa_1\text{—}(aa)_y\text{—}aa_2\text{—}(aa)_z$$
$$\quad\quad\quad\;|\quad\quad\quad\quad\;|$$
$$\quad\quad\quad N^1H\quad\quad\quad N^2H$$
$$\quad\quad\quad\;|\quad\quad\quad\quad\;|$$
$$\quad\quad\quad Ar_1\quad\quad\quad\; Ar_2$$

wherein
- $Ar_1$ and $Ar_2$ are independently selected from the group consisting of ethidium bromide, acridine, mitoxanotrone, oxazolopyridocarbazole, ellipticine, N-methyl-2, 7-diazapyrenium, and derivatives capable of intercalating a polynucleotide;
- each aa is independently an amino acid;
- x and z are integers independently selected from 1 to 100;
- y is an integer from 0 to 5;
- $aa_1$ and $aa_2$ are lysine residues; and
- $N^1$ and $N^2$ are nitrogens from the ε-amino groups of the lysine residues $aa_1$ and $aa_2$.

30. The composition of claim 17 wherein the polynucleotide-associating moiety comprises a linker strand complementary to the desired polynucleotide.

31. The composition of claim 30 wherein substantially the entire linker strand sequence is complementary to the desired polynucleotide.

32. The composition of claim 30 wherein the linker strand comprises an extension of the desired polynucleotide.

33. The composition of claim 30 wherein the linker strand has a sequence with a plurality of regions, each region complementary to a portion of the desired polynucleotide.

34. The composition of claim 30 wherein the polynucleotide-associating moiety comprises a plurality of linker strands.

35. The composition of claim 30 wherein the polynucleotide-associating moiety comprises a first linker complementary to the desired polynucleotide and a second linker complementary to the desired polynucleotide.

36. The composition of claim 17 wherein the polynucleotide-associating moiety comprises a dendrimer polycation.

37. The composition of claim 17 wherein the polynucleotide-associating moiety comprises a major- or minor-groove binder.

38. The composition of claim 37 wherein the major- or minor-groove binder is selected from the group consisting of distamycin A and Hoechst dye 33258.

39. The composition of claim 17 wherein the functional agent comprises a cell recognition agent.

40. The composition of claim 17 wherein the functional agent comprises a membrane-permeabilization agent.

41. The composition of claim 17 further comprising a membrane-permeabilizer selected from the group consisting of polylysine, polyarginine, poly (lysine-arginine), polyamines, dendrimer polycations, cationic bile salts and amphipathic peptides.

42. The composition of claim 17 wherein the functional agent comprises a subcellular-localization agent selected from the group consisting of a nuclear-localization component, a lysosomal-localization component and a mitochondrial-localization component.

43. The composition of claim 42 wherein the subcellular-localization agent is selected from the group consisting of the sequence PKKKRKV/SEQ ID NO. 1, the sequence AAFEDLRVLS/SEQ ID NO. 4, the sequence KRPRP/SEQ ID NO. 5, the sequence KFERQ/SEQ ID NO. 6 and the sequence MLSLRQSIRFFKPATR/SEQ ID NO 7.

44. The composition of claim 17 wherein the functional agent comprises a polynucleotide-masking agent.

45. The composition of claim 44 wherein the polynucleotide-masking agent comprises polyethylene glycol linked to the polynucleotide-associating moiety.

46. The composition of claim 45 comprising polyethylene glycol-bis-acridine.

47. A composition for presenting a desired polynucleotide to a subcellular component of a eukaryotic cell comprising a desired polynucleotide associated with a cationic bile salt having the formula

[Chemical structure of steroid with substituents X, Y, $CH_3$, $CH_3$, HO, and side chain $-C(=O)-N(R^3)(R^4)$]

wherein
- X and Y are independently H or OH;
- $R^3$ is hydrogen ($C_1$–$C_{10}$) alkyl or ($C_1$–$C_{10}$) alkylamine; and
- $R^4$ is a positively charged linear or branched ($C_1$–$C_{30}$) alkyl or ($C_1$–$C_{30}$) alkylamine, wherein one or more of the carbon atoms may be substituted with NR', wherein R' is H, ($C_1$–$C_{10}$)alkyl or ($C_1$–$C_{10}$) alkylamine.

48. The composition of claim 47 further comprising a lipid.

49. A composition for presenting a desired polynucleotide to a subcellular component of a eukaryotic cell comprising a desired polynucleotide associated with a polynucleotide-masking agent having the chemical formula

[Chemical structure: $R^3(R^4)N-C(=O)-(CH_2)_n-C(=O)-O-CH(R^1C(=O)-O-CH_2)-CH_2-O-P(=O)(O)-Y$]

wherein
- n is an integer of 6 to 24;
- Y is selected from the group consisting of hydroxy, ethanolamine, choline, glycerol, serine and inositol;
- $R^1$ is ($C_6$–$C_{24}$) alkyl or ($C_6$–$C_{24}$) alkenyl;
- $R^3$ is H, or ($C_1$–$C_{10}$) alkyl or ($C_1$–$C_{10}$) alkylamine; and
- $R^4$ is a positively charged linear or branched ($C_1$–$C_{30}$) alkyl or ($C_1$–$C_{30}$) alkylamine, wherein one or more of the carbon atoms may be substituted with NR', wherein R' is H or ($C_1$–$C_{10}$) alkyl or ($C_1$–$C_{10}$) alkylamine.

50. The composition of claim 49 wherein the lipid comprises lecithin acyl amine.

51. A composition for presenting a desired polynucleotide to a subcellular component of a eukaryotic cell comprising a desired polynucleotide associated with an amphipathic peptide capable of assuming a pH dependent α-helix conformation.

52. The composition of claim 51 further comprising a lipid.

53. The composition of claim 51 further comprising a polyamine.

54. The composition of 4 wherein the amphipathic peptide comprises an amphipathic peptide capable of assuming a β-pleated sheet conformation.

55. The composition of 54 wherein the β-pleated sheet amphipathic peptide has a first and second face such that the first face is positively charged and the second face is substantially neutral.

56. The composition of claim 4 wherein the amphipathic peptide comprises a cyclic peptide.

57. The composition of claim 56 wherein the cyclic peptide is selected from the group consisting of tyrocidines and gramicidin S.

58. The composition of claim 56 wherein the cyclic peptide comprises gramicidin S.

59. The composition of claim 4 comprising gramicidin S and dioleoylphosphatidylethanolamine.

60. The composition of claim 59 comprising gramicidin S and dioleoylphosphatidylethanolamine in a molar ratio of greater than about 1:1.

61. The composition of claim 60 comprising gramicidin S and dioleoylphosphatidylethanolamine in a molar ratio of greater than about 5:1.

62. The composition of claim 51 wherein the amphipathic peptide α-helix comprises a first and a second axial face such that the first face is substantially charged and the second face is substantially neutral.

63. The composition of claim 62 wherein the first face is negatively charged.

64. The composition of claim 63 wherein the amphipathic peptide comprises the sequence GALA/SEQ ID NO. 10.

65. The composition of claim 1 wherein one or more of the functional agents is operatively coupled to the desired polynucleotide by a polynucleotide-associating moiety.

66. The composition of claim 65 wherein the polynucleotide-associating moiety is selected from the group consisting of a single stranded polynucleotide linker, a dendrimer polycation, a major- or minor-groove binder, and an intercalator.

67. The composition of claim 47 further comprising dioleoylphosphatidylethanolamine.

\* \* \* \* \*

```
                       SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:1:

Pro Lys Lys Lys Arg Lys Val
1               5

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "This position is N-formyl-."

(xi) SEQUENCE DESCRIPTION: SEQ ID NO:2:

Xaa Met Leu Phe
1

(2) INFORMATION FOR SEQ ID NO:3:
```

(i) SEQUENCE CHARACTERISTICS:
    (A) LENGTH: 8 amino acids
    (B) TYPE: amino acid
    (C) STRANDEDNESS: single
    (D) TOPOLOGY: linear (xi) SEQUENCE DESCRIPTION: SEQ ID NO:3:

```
Cys Ser Gly Arg Glu Asp Val Trp
1               5
```

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:4:

```
Ala Ala Phe Glu Asp Leu Arg Val Leu Ser
1               5                   10
```

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:5:

```
Lys Arg Pro Arg Pro
1               5
```

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:6:

```
Lys Phe Glu Arg Gln
1               5
```

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:7:

```
Met Leu Ser Leu Arg Gln Ser Ile Arg Phe Phe Lys Pro Ala Thr Arg
1               5                   10                  15
```

(2) INFORMATION FOR SEQ ID NO:8:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:8:

-continued

```
Cys Gly Tyr Gly Pro Lys Lys Lys Arg Lys Val Gly Gly
1               5                   10
```

(2) INFORMATION FOR SEQ ID NO:9:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:9:

```
Cys Gly Tyr Lys Pro Lys Val Arg Gly Lys Gly Lys Gly
1               5                   10
```

(2) INFORMATION FOR SEQ ID NO:10:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:10:

```
Trp Glu Ala Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala
16              20                  25                  30
```